US010555889B2

(12) United States Patent
Parthasarathy et al.

(10) Patent No.: US 10,555,889 B2
(45) Date of Patent: Feb. 11, 2020

(54) COMPOSITIONS FOR SPORE REMOVAL

(71) Applicant: 3M INNOVATIVE PROPERTIES COMPANY, St. Paul, MN (US)

(72) Inventors: Ranjani V. Parthasarathy, Woodbury, MN (US); Ramesh C. Kumar, Woodbury, MN (US); Matthew T. Scholz, Woodbury, MN (US); Steven P. Swanson, Blaine, MN (US); Erin A. Satterwhite, Maple Grove, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 94 days.

(21) Appl. No.: 15/736,853

(22) PCT Filed: Jun. 27, 2016

(86) PCT No.: PCT/US2016/039554
§ 371 (c)(1),
(2) Date: Dec. 15, 2017

(87) PCT Pub. No.: WO2017/003923
PCT Pub. Date: Jan. 5, 2017

(65) Prior Publication Data
US 2018/0360728 A1 Dec. 20, 2018

Related U.S. Application Data

(60) Provisional application No. 62/187,372, filed on Jul. 1, 2015.

(51) Int. Cl.
| *A61K 8/81* | (2006.01) |
| *A01N 25/10* | (2006.01) |
| *A01N 31/02* | (2006.01) |
| *A01N 33/12* | (2006.01) |
| *A01N 37/02* | (2006.01) |
| *A01N 43/40* | (2006.01) |
| *A01N 43/44* | (2006.01) |
| *A01N 47/44* | (2006.01) |
| *A61K 8/49* | (2006.01) |
| *A61K 8/43* | (2006.01) |
| *A61L 2/00* | (2006.01) |
| *A61Q 17/00* | (2006.01) |
| *A61K 8/34* | (2006.01) |
| *A61K 8/41* | (2006.01) |

(52) U.S. Cl.
CPC ............ *A61K 8/8152* (2013.01); *A01N 25/10* (2013.01); *A01N 31/02* (2013.01); *A01N 33/12* (2013.01); *A01N 37/02* (2013.01); *A01N 43/40* (2013.01); *A01N 47/44* (2013.01); *A61K 8/34* (2013.01); *A61K 8/416* (2013.01); *A61K 8/43* (2013.01); *A61K 8/4926* (2013.01); *A61L 2/0088* (2013.01); *A61Q 17/005* (2013.01); *A61K 2800/412* (2013.01)

(58) Field of Classification Search
CPC ...... A61K 8/8152; A61K 8/43; A61K 8/4926; A61K 8/416; A61K 8/34; A61K 8/0241; A61K 2800/412; A01N 31/02; A01N 25/10; A01N 33/12; A01N 37/02; A01N 43/40; A01N 47/44; A61L 2/0088; A61Q 17/005
USPC .......................................................... 422/28
See application file for complete search history.

(56) References Cited

U.S. PATENT DOCUMENTS

| 4,384,097 | A | 5/1983 | Wingler |
| 5,951,993 | A | 9/1999 | Scholz |
| 6,228,354 | B1 | 5/2001 | Jeng |
| 6,383,505 | B1 | 5/2002 | Kaiser |
| 6,484,735 | B1 | 11/2002 | Gordon |
| 6,565,804 | B1 | 5/2003 | Conway |
| 6,582,711 | B1 * | 6/2003 | Asmus ............. A01N 31/02 424/405 |
| 7,576,047 | B2 | 8/2009 | Kilkenny |

(Continued)

FOREIGN PATENT DOCUMENTS

| CA | 2111932 | 6/1994 |
| CA | 2246913 | 3/1999 |

(Continued)

OTHER PUBLICATIONS

Shultz, "Effectiveness of a Lotion-Based Hand Treatment Against Spore-Forming Bacteria, Including *Clostridium Difficile*"; poster presented at APIC, Mar. 2009, vol. 37, No. 5 (Presentation No. 2-13); 1 Page.

(Continued)

*Primary Examiner* — Pamela H Weiss
(74) *Attorney, Agent, or Firm* — 3M Innovative Properties Company; Trisha D. Adamson

(57) ABSTRACT

Disclosed herein are compositions that include at least about 85 wt % of a hydroalcoholic solution that includes at least about 1 wt % water; and about 30 to about 85 wt % of at least one C1 to C4 alkyl alcohol based on the total weight of the hydroalcoholic solution; and acrylate copolymer particles dispersed in the hydroalcoholic solution, the acrylate copolymers particles being the reaction product of a reaction mixture, the reaction mixture including monomers, the monomers including from about 5 wt % to about 50 wt % of at least one high Tg monomer; and from about 20 w % to about 80 wt % of at least one low Tg monomer where the wt % of the low and high Tg monomers are with respect to the total weight of the monomers in the reaction mixture, wherein the particles have a number average diameter of at least about 100 nm.

19 Claims, No Drawings

(56) References Cited

U.S. PATENT DOCUMENTS

| | | | | |
|---|---|---|---|---|
| 8,062,649 | B2* | 11/2011 | Asmus | A01N 31/02 424/405 |
| 8,623,935 | B2* | 1/2014 | Hobbs | A01N 25/02 523/122 |
| 2003/0215418 | A1* | 11/2003 | Asmus | A01N 31/02 424/78.35 |
| 2005/0261159 | A1 | 11/2005 | Parris | |
| 2006/0030686 | A1* | 2/2006 | Lion | A61K 8/8152 526/319 |
| 2006/0141017 | A1 | 6/2006 | Kling | |
| 2007/0054827 | A1 | 3/2007 | Cheung | |
| 2007/0129641 | A1 | 6/2007 | Sweeney | |
| 2007/0184016 | A1 | 8/2007 | Macinga | |
| 2007/0244027 | A1 | 10/2007 | Sivik | |
| 2007/0274926 | A1* | 11/2007 | Fuls | A01N 37/04 424/45 |
| 2007/0281999 | A1* | 12/2007 | Fox | A01N 31/02 514/557 |
| 2008/0044479 | A1 | 2/2008 | Stack | |
| 2008/0102053 | A1 | 5/2008 | Childers | |
| 2008/0108704 | A1* | 5/2008 | Asmus | A01N 31/02 514/635 |
| 2009/0301519 | A1 | 12/2009 | Aubay | |
| 2010/0136069 | A1 | 6/2010 | Deckner | |
| 2011/0152925 | A1 | 6/2011 | Schorr | |
| 2013/0302385 | A1* | 11/2013 | Muenz | A61K 8/91 424/401 |
| 2014/0227210 | A1 | 8/2014 | Farcet | |
| 2014/0261454 | A1 | 9/2014 | Dokken | |

FOREIGN PATENT DOCUMENTS

| | | | |
|---|---|---|---|
| CA | 2621986 | 8/2008 | |
| CN | 101463303 | 6/2009 | |
| DE | 102004058143 | 5/2006 | |
| EP | 0027221 | 4/1981 | |
| EP | 0971997 | 1/2000 | |
| GB | 720574 | 12/1954 | |
| JP | 4234986 | 8/1992 | |
| KR | 2001-0110625 | 12/2001 | |
| KR | 2003-0085436 | 11/2003 | |
| WO | WO 2000-30599 | 6/2000 | |
| WO | WO 2001-41727 | 6/2001 | |
| WO | WO 2003-066001 | 8/2003 | |
| WO | WO-2005079765 A1 * | 9/2005 | ........... A61K 9/0014 |
| WO | WO 2006-013315 | 2/2006 | |
| WO | WO 2006-084251 | 8/2006 | |
| WO | WO 2007-100653 | 9/2007 | |
| WO | WO 2008-003632 | 1/2008 | |
| WO | WO 2009-112843 | 9/2009 | |

OTHER PUBLICATIONS

International Search report for PCT International Application No. PCT/US2016/039554 dated Oct. 17, 2016, 5 pages.

* cited by examiner

COMPOSITIONS FOR SPORE REMOVAL

CROSS REFERENCE TO RELATED APPLICATIONS

This application is a national stage filing under 35 U.S.C. 371 of PCT/US2016/039554, filed Jun. 27, 2016, which claims the benefit of U.S. Provisional Application No. 62/187,372, filed Jul. 1, 2015, the disclosures of which are incorporated by reference in their entirety herein.

FIELD

The present disclosure relates to compositions for and methods of removing spores from surfaces.

BACKGROUND

There is a great deal of interest and urgency in preventing the spread of *C. difficile*, particularly in medical settings such as hospitals. Patients in a hospital setting often times develop *C. difficile* infections during or shortly after a course of antibiotics. While it is relatively easy to kill the vegetative form of *C. difficile*, the spore form of *C. difficile*, can be very difficult to kill. New technologies are therefore needed to address the problem of preventing the spread of *C. difficile*, between patients, health care workers, and the environment.

SUMMARY

Disclosed herein are compositions that include at least about 85 wt % of a hydroalcoholic solution based on the total weight of the composition, the hydroalcoholic solution includes at least about 1 wt % water based on the total weight of the hydroalcoholic solution; and about 30 to about 85 wt % of at least one C1 to C4 alkyl alcohol based on the total weight of the hydroalcoholic solution; and acrylate copolymer particles dispersed in the hydroalcoholic solution, the acrylate copolymer particles being the reaction product of a reaction mixture, the reaction mixture including monomers, the monomers including from about 5 wt % to about 50 wt % of at least one high Tg monomer where the wt % of the at least one high Tg monomer is with respect to the total weight of the monomers in the reaction mixture; and from about 20 wt % to about 80 wt % of at least one low Tg monomer where the wt % of the at least one low Tg monomer is with respect to the total weight of the monomers in the reaction mixture, wherein the particles have a number average diameter of at least about 100 nm.

Also disclosed are compositions that include at least about 1 wt % water based on the total weight of the composition; from about 30 wt % to about 98 wt % of at least one $C_1$ to $C_4$ alkyl alcohol based on the total weight of the composition; and not greater than about 5 wt % acrylate copolymer particles based on the total weight of the composition, where the acrylate copolymer particles are dispersed in the water and alcohol, the acrylate copolymer particles being the reaction product of a reaction mixture, the reaction mixture including monomers, the monomers including from about 5 wt % to about 50 wt % of at least one high Tg monomer, where the wt % of the at least one high Tg monomer is with respect to the total weight of the monomers in the reaction mixture; and from about 20 wt % to about 80 wt % of at least one low Tg monomer where the wt % of the at least one low Tg monomer is with respect to the total weight of the monomers in the reaction mixture and wherein the particles have a number average diameter of at least 100 nm.

Also disclosed are methods of dislodging at least one spore from a surface, the methods including contacting the surface with a composition, the composition including at least about 60 wt % of at least one $C_1$ to $C_4$ alkyl alcohol based on the total weight of the composition; and acrylate copolymer particles dispersed in the alcohol; and subjecting the surface in contact with the composition to mechanical action.

Also disclosed are methods of removing at least one spore from a surface, the methods including contacting the surface with a composition, the composition including at least about 85 wt % of a hydroalcoholic solution based on the total weight of the composition, the hydroalcoholic solution including at least about 1 wt % water based on the weight of the hydroalcoholic solution, and about 30 wt % to about 95 wt % of at least one $C_1$ to $C_4$ alkyl alcohol based on the total weight of the hydroalcoholic solution; and acrylate copolymer particles dispersed in the hydroalcoholic solution, the acrylate copolymer particles being the reaction product of a reaction mixture, the reaction mixture including monomers, the monomers including from about 5 wt % to about 50 wt % of at least one high Tg monomer where the wt % of the at least one high Tg monomer is with respect to the total weight of the monomers in the reaction mixture; and from about 20 w % to about 80 wt % of at least one low Tg monomer where the wt % of the at least one low Tg monomer is with respect to the total weight of the monomers in the reaction mixture, wherein the acrylate copolymer particles have an average diameter of at least about 100 nm.

The above summary of the present disclosure is not intended to describe each disclosed embodiment or every implementation of the present disclosure. The description that follows more particularly exemplifies illustrative embodiments. In several places throughout the application, guidance is provided through lists of examples; examples can be used in various combinations. In each instance, the recited list serves only as a representative group and should not be interpreted as an exclusive list.

DETAILED DESCRIPTION

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, "top" and "bottom" (or other terms like "upper" and "lower") are utilized strictly for relative descriptions and do not imply any overall orientation of the article in which the described element is located.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. For example, a conductive trace that "comprises" silver may be a conductive trace that "consists of" silver or that "consists essentially of" silver.

As used herein, "consisting essentially of," as it relates to a composition, apparatus, system, method or the like, means that the components of the composition, apparatus, system, method or the like are limited to the enumerated components and any other components that do not materially affect the basic and novel characteristic(s) of the composition, apparatus, system, method or the like.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Use of "first," "second," etc. in the description above and the claims that follow is not intended to necessarily indicate that the enumerated number of objects are present. For example, a "second" substrate is merely intended to differentiate from another substrate (such as a "first" substrate). Use of "first," "second," etc. in the description above and the claims that follow is also not necessarily intended to indicate that one comes earlier in time than the other.

Disclosed herein are compositions that include an acrylate copolymer and alcohol. Disclosed compositions can also be described as including a hydroalcoholic solution and an acrylate copolymer. Disclosed compositions or formulations can include an acrylate copolymer that includes at least one component having a low glass transition temperature (Tg) and at least one component having a high Tg, in an alcohol containing medium. As used herein the term high Tg component or low Tg component refers to the glass transition temperature of a homopolymer formed from that component. For example, N-vinyl pyrrolidone would be a high Tg component since polyvinyl pyrrolidone has a Tg of 54° C. while isooctylacrylate (IOA) is a low Tg component (monomer) since a poly (IOA) polymer has a Tg of −58° C. The component or components having a low Tg can be referred to as a low Tg component and the component or components having a high Tg can be referred to as a high Tg component. The low Tg component can be formed from a low Tg monomer and the high Tg component can be formed from a high Tg monomer. Disclosed compositions may be useful for removing spores from surfaces. As used herein the term spore refers to bacterial spores. It is thought, but not relied upon that the low Tg component may offer adhesion to the spore and the high Tg component allows for the release of the spore from the skin. Spores can adhere strongly to surfaces such as skin and can be very difficult to remove.

Compositions for removing spores from surfaces are important because there is a great deal of interest and urgency in preventing the spread of C. difficile, particularly in medical settings such as hospitals. Patients in a hospital setting often times develop C. difficile infections during or shortly after a course of antibiotics. While it is relatively easy to kill the vegetative form of C. difficile, the spore form of C. difficile, can be very difficult to kill. New technologies are needed to address the problem of preventing the spread of C. difficile, between patients, health care workers, and the environment.

Previously utilized compositions are numerous, and include bleach, alcohol foams and gels, for example. Bleach is a commonly used sporicide, and is effective and recommended by the Centers for Disease Control (CDC) for use in a hospital setting to disinfect environmental surfaces. However, bleach cannot be utilized by patients and health care workers on their skin. Currently, alcohol foams and gels are used by most healthcare workers. These solutions are however not effective at eradicating C. difficile spores. The CDC recommendation for healthcare workers and patients affected by C. difficile is normal hand washing with soap, water and paper towel. However, it is not always convenient to implement this solution for a health care worker due to the lack of nearby sink access and time. Further, this is an inconvenient solution for the caregiver to implement on a patient with limited mobility.

Dilute bleach or hydrogen peroxide and similar products have been used on hands and have demonstrated the ability to kill spores. While spore kill is important, it is not clear that these solutions are safe for repeated use. For example, a health care worker may wash their hands 30-50 times in a single day, and some up to 75 times a day or more as they wash in and out of patient rooms. Long term toxicity and destruction of host tissues would be a concern for these solutions.

It is therefore extremely important to develop compositions that are safe for repeated use on the skin; reduce spores to a level equivalent to that of the CDC recommended protocol (soap, water and paper towel); and have the ability to kill vegetative bacteria rapidly. Alcohol is used to kill vegetative cells rapidly, but does not kill spores. It would also be useful to have compositions that could be used in various formats including wipes, gels, sprays, etc. Compositions that could be utilized for various aspects of patient care such as hand sanitization, patient bathing, and pre-op care could also be greatly beneficial. Compositions that could be used for patient care as well as environmental cleaning; for example, fragile or expensive equipment/surfaces in a hospital room that may warrant the use of less aggressive tissue friendly chemicals could also be quite useful to the medical community.

Disclosed compositions overcome spore adhesion to surfaces, such as the skin, allowing for the spores to be dispersed and transferred into a woven, knitted, or nonwoven wipe surface, for example. Disclosed compositions can include alcohol and acrylate copolymer. In some embodiments disclosed compositions can include a hydroalcoholic solution and an acrylic copolymer. In some embodiments, disclosed compositions can be described as stable dispersions. A "stable dispersion" as utilized herein refers to a composition in which particles remain dispersed in solution without falling out or "crashing out" of solution (e.g. flocculating or settling).

The phrase "hydroalcoholic solution" refers to a composition or solution that includes at least water and an alcohol. In some embodiments, a useful hydroalcoholic solution can include not less than 1 percent by weight (wt %) water, or in some embodiments not less than 5 wt % water based on the total weight of the hydroalcoholic solution. In some embodiments, a useful hydroalcoholic solution can include not greater than 15 wt % water based on the total weight of the hydroalcoholic solution. In some embodiments, a useful hydroalcoholic solution can include not less than 30 wt % alcohol based on the total weight of the hydroalcoholic solution. In some embodiments a useful hydroalcoholic solution can include not greater than 85 wt % alcohol, not greater than 95 wt % alcohol, or not greater than 99% alcohol based on the total weight of the hydroalcoholic solution.

In some embodiments, the amount of alcohol in the entire composition can also be considered (as opposed to the amount of alcohol in the hydroalcoholic solution). The amount of alcohol in the entire composition may be relevant because the total alcohol content can provide bacteria killing properties. In some embodiments, disclosed compositions can have not less than 30 wt % alcohol based on the total weight of the entire composition. In some embodiments, disclosed compositions can have not less than 60 wt % alcohol in the composition, in some embodiments not less than 61 wt % alcohol in the composition, or in some embodiments not less than 70 wt % alcohol in the composition based on the total weight of the entire composition. In some embodiments, disclosed compositions can have not greater than 85 wt % alcohol, not greater than 95 wt % alcohol, or not greater than 98% alcohol based on the total weight of the entire composition. In some embodiments disclosed compositions can have from 60 wt % to 70 wt % alcohol in the entire composition based on the total weight of the entire composition. In some embodiments, disclosed compositions can have from 30 wt % to 85 wt % alcohol in the entire composition based on the total weight of the entire composition. In some embodiments, the entire composition may have at least 1 wt % water, at least 10 wt % water, or in some embodiments at least 11 wt % water based on the total weight of the entire composition.

Any kind of alkyl monofunctional alcohol can be utilized as the alcohol(s) in a hydroalcoholic solution. In some embodiments, a lower hydrocarbon chain alcohol such as a $C_2$-$C_5$ alcohol can be utilized. In some embodiments the alcohol is chosen from ethanol and isopropanol, and in some embodiments ethanol. Ethanol may be useful because it may provide a broad spectrum and quick kill of microbes and an odor acceptable to consumers such as doctors, nurses and clinicians. Propyl alcohol (1-propanol) may also be used. A blend of two or more lower alcohols may also be utilized. The lower alcohols may be denatured, such as for example, denatured ethanol including SDA-3C (commercially available from Eastman Chemical, Kingsport, Tenn.). Co-solvents may be further included in the composition with the lower alcohol. Considering likely applications contemplated, suitable co-solvents can include for example acetone, hydrocarbons such as isooctane, glycols, ketones, ethers, and short chain esters.

In some embodiments, the hydroalcoholic solution can be at least 85% by weight (wt %) of the entire composition based on the total weight of the entire composition.

Disclosed compositions also include an acrylate copolymer. It should also be noted that more than one copolymer can be utilized herein. A copolymer can be formed by copolymerization of at least 2 monomers to form a block or random copolymer. A blend of two homopolymer components in a ratio to provide a similar Tg to that of an acrylate copolymer produced from two monomers is not considered a copolymer as used in disclosed compositions. Copolymer particles as that phrase is utilized herein are preferably formed from a single copolymer but blends of two or more copolymers or blends with other homopolymers may be useful. Properties such as shear and adhesion properties, for example, of a blend designed to give a particular Tg may be different than the properties found in a disclosed copolymer having the same particular overall Tg.

An acrylate copolymer as described herein includes at least one acrylate component, or was polymerized from a reaction mixture containing at least one component or monomer, for example at least one acrylic containing monomer. More specifically, disclosed compositions can include acrylate copolymer particles. The acrylate copolymer or acrylate copolymer particles can be described as the reaction product of at least a low Tg monomer and a high Tg monomer. The acrylate copolymer particles can also be described by their particle size. The acrylate copolymer or copolymer particles can be described as the reaction product of a reaction mixture that includes at least one component, e.g., at least one low Tg monomer, at least one high Tg monomer, or combinations thereof, etc.

The amount of the acrylate copolymer in disclosed compositions can also be indicated. In some embodiments, disclosed compositions can include not less than 0.25 wt % acrylate copolymer, not less than 0.5 wt % acrylate copolymer, or not less than 1 wt % acrylate copolymer, or in some embodiments not less than 2 wt % acrylate copolymer based on the total weight of the entire composition. In some embodiments, disclosed compositions can include not greater than 15 wt % acrylate copolymer, not greater than 5 wt % acrylate copolymer, or in some embodiments not greater than 4 wt % based on the total weight of the entire composition. In some embodiments, disclosed compositions can include from 1 wt % to 5 wt % acrylate copolymer, or in some embodiments from 2 wt % to 4 wt % acrylate copolymer based on the total weight of the entire composition.

Acrylate copolymer or more specifically acrylate copolymer particles in disclosed compositions can be described by the monomers used to form the acrylate copolymer. In some embodiments at least one or more monomers having a high Tg and at least one or more monomers having a low Tg can be utilized to form the acrylate copolymer in disclosed compositions. As used herein, a value for the Tg of a monomer is the Tg of a homopolymer polymerized from the particular monomer. The low Tg monomer forms the low Tg component of the acrylate copolymer and the high Tg monomer forms the high Tg component of the acrylate copolymer.

In some embodiments, the at least one or more monomers having a high Tg can be a monomer(s) having a Tg of not less than 40° C., or in some embodiments not less than 60° C. for example. In some embodiments, the at least one or more monomers having a high Tg can be a monomer(s) having a Tg of not greater than 150° C., or not greater than 125° C. for example. In some embodiments, the at least one or more monomers having a high Tg can be a monomer(s) having a Tg from 40° C. to 150° C., or in some embodiments from 60° C. to 125° C., for example. In some embodiments, a high Tg monomer or component can have a Tg of 105° C. In some embodiments, the at least one or more monomers having a low Tg can be a monomer(s) having a Tg of not greater than −30° C., or in some embodiments not greater than −20° C. for example. In some embodiments, the at least one or more monomers having a low Tg can be a monomer(s) having a Tg of not less than −60° C., or not less than −55° C. for example. In some embodiments, the at least one or more monomers having a low Tg can be a monomer(s) having a Tg from −60 to −20° C., for example. In some embodiments, a low Tg monomer or component can have a Tg of −50° C.

Low Tg and high Tg monomers components can also be described by the number of carbons in the monomer. For example, low Tg monomers can include monomers having not less than four (4) alkyl chain carbons. In some embodiments, low Tg monomers can have not greater than 10 carbons. For example, high Tg monomers can include monomers having not greater than three (3) carbons. In some embodiments, high Tg monomers can have not less than one (1) carbon.

Low Tg and high Tg monomers can also be described structurally. In some embodiments, high Tg monomers can be those of formula I below:

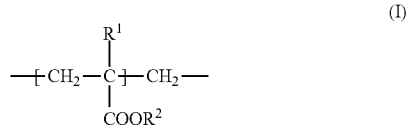

where $R^1$ is H or $-CH_3$, and $R^2$ is $-CH_3$ or $-CH_2CH_3$. In some embodiments, low Tg monomers can be those of formula II below:

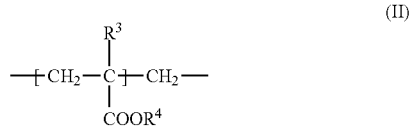

where $R^3$ is H or $-CH_3$, $R^4$ is $-CH_2(CH_2)_xCH_3$ where x is an integer from one (1) to twelve (12) and the alkyl chain can be straight or branched. In some embodiments, x can be an integer from two (2) to six (6). In some embodiments, x can be six (6) and the alkyl can be a branched alkyl.

As such, acrylate copolymers formed from at least monomers of formula I and II can be described as follows in formula III.

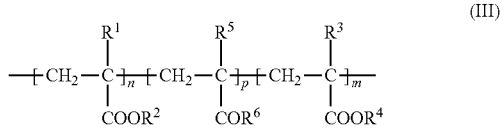

where $R^1$ is H or $-CH_3$, $R^2$ is H, $-CH_3$ or $-CH_2CH_3$, $R^3$ is H or $-CH_3$, $R^4$ is $-CH_2(CH_2)_xCH_3$ where x is an integer from one (1) to eight (8) and the alkyl chain can be straight or branched, $R^5$ is H or $-CH_3$, $R^6$ is OH, $NH_2$, $NHCH_3$, $N(CH_3)_2$, $-OCH_2CH_2OH$, m is an integer from 20 to 1,500,000, n is an integer from 20 to 1,500,000, p is an integer from zero (0) to 1,500,000, with the proviso that m is greater than n, and both m and n are greater than p. In some embodiments $R^1$ is $-CH_3$, $R^2$ is $-CH_3$ or $-CH_2CH_3$, and $R^3$ is H. In some embodiments, the optional monomer (the middle structure in the polymeric chain above) can be derived from an acrylamide monomer, an acrylic acid monomer, a pyrrolidone monomer, a N-vinyl pyrrolidone monomer, or other high Tg monomer, or any combination thereof. It should be noted that the order of the monomers listed in the formula above are for illustration purposes only. The monomers may occur in any order in a random or block fashion.

In some illustrative embodiments, low Tg monomers can include for example 2-ethylhexyl acrylate (EHA) that has a Tg of −50° C., butyl acrylate (BA) that has a Tg of −54° C., and isooctylacrylate (IOA) that has a Tg of −58° C., or combinations thereof. In some illustrative embodiments, high Tg monomers can include, for example, methyl methacrylate (MMA) that has a Tg of 105° C., acrylic acid (AA) that has a Tg of 105° C., and hydroxyethylmethacrylate (HEMA) that has a Tg of 55° C. Specific examples of potential polymers that can be utilized as or in useful copolymer particles can include, for example acrylates such as Dermacryl C (polymerized from a mixture of EHA, MMA and AA) commercially available from Akzo Personal Care and Balance 0/55 (polymerized from a mixture of BA and MMA) previously commercially available from Akzo Personal Care.

Copolymer particles useful herein can also include optional components or optional monomers. Some such optional components can include, other polymers and/or monomers that may be used to form copolymer particles. If polymers are utilized to form the copolymer particles, the weight of such polymers are considered monomers when determining the total weight of the reaction mixture. Generally, the composition of the acrylate copolymer particles can include but are not limited to the following polymers: acrylates, polyacrylates, urethanes, polyurethanes, polyesters, polysaccharides, polyolefins, polyamides, polyimides, polyethylenes, polyalkyls, polyols, polystyrenes, polyethers, polyhalides, polynitriles, cellulosics, proteins, triglycerides, polyamino acids, silicone polymers and resins, esters derived from rosin, epoxy resins, shellacs, latexes, or any combinations thereof.

Specific examples of components than can be included in acrylate copolymer particles can include for example PVP K Series (polyvinylpyrrolidone) from International Specialty Products, Luviskol K Series (polyvinylpyrrolidone) from BASF, PVP/VA (vinyl acetate/vinyl pyrrolidone copolymer) from International Specialty Products, for example grades W-735 and S-630, Gantrez (copolymers of methyl vinyl ether/maleic anhydride) from International Specialty Products, Carboset Series (acrylate copolymer) from BF Goodrich, Resyn Series (vinyl acetate/crotonate copolymers) from National Starch and Chemical Corporation, Versatyl Series (acrylate/octylacrylamide copolymers) from National Starch and Chemical Corporation. Airvol (polyvinylalcohol copolymer) from Air Products and Chemicals, for example all commercially available grades like Airvol 103, Airvol 325, Airvol 540, Airvol 523S, Vinex copolymer of vinyl alcohol and poly(oxyalkylene)acrylate from Air Products and Chemicals, for example all commercially available grades such as Vinex 1003, Vinex 2034, Vinex 2144, Vinex 2019, PEOX (polyethyloxazoline) from Polymer Chemistry Innovations, Covacryl A15 and Covacryl E14 by Wackherr, acrylates/ethylhexyl acrylate copolymers (Daitosol 5000SJ by Daito Kasei), butyl acrylate/hydroxypropyl dimethicone acrylate copolymers (Granacrysil BAS by Grant Industries, Inc.), acrylates/$C_{12}$-$C_{22}$ alkylmethacrylate copolymers (Allianz OPT by ISP), isododecane and acrylates copolymers (Giovarez AC-5099M by Phoenix), acrylates/octylacrylamide copolymers (Dermacryl-79 by National Starch & Chemical Company), and sodium polystyrene sulfonates (Flexan 130 by National Starch & Chemical Company), Ganex (vinyl pyrolidinone/Eicosenene copolymer) from ISP, Polectron (vinylpyrrolidinone/styrene copolymer emulsion) from ISP.

Although not bound by any particular theory, suitable components of the acrylate polymers may be selected on the basis of their properties and/or structure. Some acrylates are insoluble in water in their free acid form and, thus, are water resistant. If such water-insoluble acrylates are neutralized with a base to their salt form, water solubility can be significantly increased. The solubility profile of an acrylate polymer may be impacted by the incidence of polar or ionic groups such as acid groups therein. The properties may also be dependent on the kind of base that is used to neutralize the acid functionalities in the polymer. For example, an acrylate polymer with triethanolamine as a neutralizer may have different properties from one neutralized using sodium hydroxide. In one embodiment, an acrylate copolymer may include an acrylate polymer with an alkyl or aralkyl quaternary ammonium salt such as cetyl pyridinium chloride to form an ionic complex with all or part of the acid functionalities. In addition, the optional surfactants that may be used to keep the acrylate emulsion stable may play a role in the final formulation.

Anionic monomers such as acrylic acid (AA) monomer in relatively small concentrations can also be included in reaction mixtures or disclosed compositions. The acid functionalities thereof can be complexed using, for example, cationic compounds such as cationic antimicrobials (e.g. benzalkonium chloride, cetylpyridinium chloride, etc). In addition, primary, secondary, and tertiary amines can be used to neutralize acidic monomers. These amines also may optionally provide antimicrobial activity (e.g. lauryl arginate, chlorhexidine, etc.)

In some embodiments Dermacryl C, Balance O/55 and Avalure 210 may be utilized. Acidic functionalities in these copolymers that are partially neutralized may be useful for spore removal. These particular copolymers form soft flexible coatings that are water-resistant. These polymers have also been designed for removal using soap and water in cosmetic applications. Disclosed compositions may also be advantageously removed from the surface. As a possible use of disclosed compositions is for the skin it could be advantageous to have acceptable cosmetic appeal since there may be repeated contact with hands for example. For instance, undesirable characteristics could include "balling" of the formulation, peeling of dried formulation, causing the skin to feel dry or chapped, etc. Excipients could optionally be added to improve cosmetic properties such as those described above; however, one would have to consider whether such excipients could have a negative effect on the spore removal performance as well as possible antibacterial nature of the composition. The addition of room temperature waxes such as stearic acid, stearyl alcohol, cetyl palmitate, etc. or silicone based emollients such as dimethicone copolyols and dimethicones, for example, may aid in improving such properties.

Useful acrylate copolymers are the reaction product of at least one high Tg monomer and at least one low Tg monomer. In some embodiments, the amount of the at least one low Tg monomer is greater than the amount of the at least one high Tg monomer. In some embodiments the acrylate copolymer is the reaction product of at least 5 wt % of at least one high Tg monomer, at least 10 wt % of at least one high Tg monomer, at least 15 wt % of at least one high Tg monomer, or at least 20 wt % of a high Tg monomer based on the total weight of the reaction mixture that forms the acrylate copolymer. In some embodiments the acrylate copolymer is the reaction product of not greater than 40 wt % of at least one high Tg monomer, not greater than 50 wt % of at least one high Tg monomer, not greater than 60 wt % of a high Tg monomer, not greater than 80 wt % of a high Tg monomer, or in some embodiments not greater than 85 wt % of a high Tg monomer based on the total weight of the reaction mixture that forms the acrylate copolymer. In some embodiments, the acrylate copolymer is the reaction product of from 5 wt % to 80 wt % of at least one high Tg monomer, from 5 wt % to 50 wt % of at least one high Tg monomer, from 20 wt % to 50 wt % of at least one high Tg monomer, or from 20 wt % to 60 wt % of a high Tg monomer based on the total weight of the reaction mixture that forms the acrylate copolymer.

In some embodiments the acrylate copolymer is the reaction product of at least 10 wt % of at least one low Tg monomer, at least 20 wt % of at least one low Tg monomer, at least 25 wt % of at least one low Tg monomer, at least 40 wt % of at least one low Tg monomer, or at least 60 wt % of at least one low Tg monomer based on the total weight of the reaction mixture that forms the acrylate copolymer. In some embodiments the acrylate copolymer is the reaction product of not greater than 80 wt % of at least one low Tg monomer, not greater than 85 wt % of at least one low Tg monomer, or not greater than 90 wt % of at least one low Tg monomer based on the total weight of the reaction mixture that forms the acrylate copolymer. In some embodiments, the acrylate copolymer is the reaction product of from 40 wt % to 90 wt % of at least one low Tg monomer, from 20 wt % to 80 wt % of at least one low Tg monomer, from 40 wt % to 80 wt % of at least one low Tg monomer, or from 60 wt % to 80 wt % of at least one low Tg monomer based on the total weight of the reaction mixture that forms the acrylate copolymer.

In some embodiments, the acrylate copolymer or the reaction mixture that forms the acrylate copolymer can be described by the total minimum amount of the at least one low Tg and the at least one high Tg monomer contained therein. For example a reaction mixture can include at least 25 wt % of all low Tg and high Tg monomers in a reaction mixture, or include at least 30 wt % of all low Tg and high Tg monomers in a reaction mixture based on the total of the monomers in the reaction mixture.

Acrylate copolymers in disclosed compositions may be more specifically described as acrylate copolymer particles dispersed in the hydroalcoholic vehicle. As such, the acrylate copolymer particles can be described by their particle size. In some embodiments, acrylate copolymer particles can have a number average diameter of not less than 100 nanometers (nm), or in some embodiments not less than 200 nm. In some embodiments, acrylate copolymer particles can have a number average diameter of not greater than 500 nm. The size of the acrylate copolymer particles may be relevant in effecting or at least partially effecting spore removal. In some embodiments, acrylate copolymer particles may have a number average diameter in the micrometer (or micron) range.

Disclosed compositions can also include one or more other optional components. For example surfactants including anionic surfactants, amphoteric surfactants, nonionic surfactants or combinations thereof may be included in disclosed compositions. Surfactants, if utilized, may be used to stabilize the dispersed particles in the composition for example. In some embodiments, anionic surfactants or nonionic surfactants can optionally be utilized in disclosed compositions.

Anionic surfactants can include, but are not limited to, sarcosinates, glutamates, alkyl sulfates, sodium or potassium alkyleth sulfates, ammonium alkyleth sulfates, ammonium laureth-n-sulfates, laureth-n-sulfates, isethionates, alkyl and aralkyl glycerylether sulfonates, alkyl and aralkyl sulfosuccinates, alkylglyceryl ether sulfonates, alkyl phosphates, aralkyl phosphates, alkylphosphonates, and aralkylphosphonates. These anionic surfactants may have a metal or organic ammonium counterion. In some embodiments anionic surfactants selected from sulfonates and sulfates, and phosphonates and phosphates may be utilized in disclosed compositions.

Suitable anionic surfactants can include sulfonates and sulfates such as alkyl sulfates, alkylether sulfates, alkyl sulfonates, alkylether sulfonates, alkylbenzene sufonates, alkylbenzene ether sulfates, alkylsulfoacetates, secondary alkane sulfonates, secondary alkylsulfates, and the like. Many of these can be represented by the formulas: R14-$(OCH_2CH_2)n(OCH(CH_3)CH_2)_p$-$(Ph)_a$-$(OCH_2CH_2)_m$—$(O)_b$—$SO_3$-M+ and R14-CH[$SO_3$-M+]-R15 wherein: a and b=0 or 1; n, p, and m=0-100 (in some embodiments 0-20, and in some embodiments 0-10); R14 and R15 are (C1-C12)alkyl group (saturated straight, branched, or cyclic group) that may be optionally substituted by N, O, or S atoms or hydroxyl, carboxyl, amide, or amine groups provided at least one R14 or R15 is at least C8; Ph=phenyl; and M is a cationic counterion such as H, Na, K, Li, ammonium, or a protonated tertiary amine such as triethanolamine or a quaternary ammonium group.

In the formula above, the ethylene oxide groups (i.e., the "n" and "m" groups) and propylene oxide groups (i.e., the "p" groups) can occur in reverse order as well as in a random, sequential, or block arrangement. In some embodiments for this class, R1 can include an alkylamide group such as R16-C(O)N(CH3)$CH_2CH_2$— as well as ester groups such as —OC(O)—$CH_2$— wherein R16 is a (C8-C22)alkyl group (branched, straight, or cyclic group). Examples include, but are not limited to: alkyl ether sulfonates such as lauryl ether sulfates such as POLYSTEP B12 (n=3-4, M=sodium) and B22 (n=12, M=ammonium) available from Stepan Company, Northfield, Ill. and sodium methyl taurate (available under the trade designation NIKKOL CMT30 from Nikko Chemicals Co., Tokyo, Japan); secondary alkane sulfonates such as Hostapur SAS which is a sodium salt of a secondary alkane sulfonate.

Examples can include, for example (C14-C17)secondary alkane sulfonates (alpha-olefin sulfonates) available from Clariant Corp., Charlotte, N.C.; methyl-2-sulfoalkyl esters such as sodium methyl-2-sulfo(C12-16)ester and disodium 2-sulfo(C12-C16)fatty acid available from Stepan Company under the trade designation ALPHASTEP PC-48; alkylsulfoacetates and alkylsulfosuccinates available as sodium laurylsulfoacetate (under the trade designation LANTHANOL LAL) and disodiumlaurethsulfosuccinate (STEPANMILD SL3), both from Stepan Company; alkylsulfates such as ammoniumlauryl sulfate commercially available under the trade designation STEPANOL AM from Stepan Company; dialkylsulfosuccinates such as dioctylsodiumsulfosuccinate available as Aerosol OT from Cytec Industries.

Suitable anionic surfactants can also include phosphates such as alkyl phosphates, alkylether phosphates, aralkylphosphates, and aralkylether phosphates. Many may be represented by the formula: [R14-$(Ph)_a$-O$(CH_2CH_2O)$n $(CH_2CH(CH3)O)_p]_q$—P(O)[O-M+]$_r$ wherein: Ph, R14, a, n, p, and M are defined above; r is 0-2; and q=1-3; with the proviso that when q=1, r=2, and when q=2, r=1, and when q=3, r=0. As above, the ethylene oxide groups (i.e., the "n" groups) and propylene oxide groups (i.e., the "p" groups) can occur in reverse order as well as in a random, sequential, or block arrangement. Examples can include a mixture of mono-, di- and tri-(alkylalkoxylate)-o-phosphoric acid esters such as trilaureth-4-phosphate commercially available under the trade designation HOSTAPHAT 340KX from Clariant Corp., as well as PPG-5 ceteth 10 phosphate available under the trade designation CRODAPHOS SG from Croda Inc., Parsipanny, N.J., and mixtures thereof.

Trade names for anionic surfactants include Rhodocal DS-10, Stepan Mild, and Complemix.

Amphoteric Surfactants. Surfactants of the amphoteric type include surfactants having tertiary amine groups, which may be protonated, as well as quaternary amine containing zwitterionic surfactants. In some embodiments ammonium carboxylates and ammonium sulfonates may be utilized.

The ammonium carboxylate class of surfactants can be represented by the following formula: R17-(C(O)—NH)a-R18-N+$(R19)_2$-R20-COO— wherein: a=0 or 1; R17 is a (C7-C21)alkyl group (saturated straight, branched, or cyclic group), a (C6-C22)aryl group, or a (C6-C22)aralkyl or alkaryl group (saturated straight, branched, or cyclic alkyl group), wherein R17 may be optionally substituted with one or more N, O, or S atoms, or one or more hydroxyl, carboxyl, amide, or amine groups; R19 is H or a (C1-C8) alkyl group (saturated straight, branched, or cyclic group), wherein R19 may be optionally substituted with one or more N, O, or S atoms, or one or more hydroxyl, carboxyl, amine groups, a (C6-C9)aryl group, or a (C6-C9)aralkyl or alkaryl group; and R18 and R20 are each independently a (C1-C10) alkylene group that may be the same or different and may be optionally substituted with one or more N, O, or S atoms, or one or more hydroxyl or amine groups. In some embodiments, in the formula above, R17 is a (C1-C18)alkyl group, R19 is a (C1-C2)alkyl group which can be substituted with a methyl or benzyl group and in some embodiments with a methyl group. When R19 is H it is understood that the surfactant at higher pH values could exist as a tertiary amine with a cationic counterion such as Na, K, Li, or a quaternary amine group. Examples of such amphoteric surfactants include, but are not limited to: certain betaines such as cocobetaine and cocamidopropyl betaine (commercially available under the trade designations MACKAM CB-35 and MACKAM L from McIntyre Group Ltd., University Park, Ill.); monoacetates such as sodium lauroamphoacetate; diacetates such as disodium lauroamphoacetate; amino- and alkylamino-propionates such as lauraniinopropionic acid (commercially available under the trade designations MACKAM IL, MACKAM 2L, and MACKAM 15 IL, respectively, from McIntyre Group Ltd.).

The ammonium sulfonate class of amphoteric surfactants are often referred to as "sultaines" or "sulfobetaines" and can be represented by the following formula: RI7-(C(O)—NH)$_a$—R18-N+$(RI9)_2$-R20-$SO_3$ wherein R17-R20 and "a" are defined above. Examples include cocamidopropylhydroxysultaine (commercially available as MACKAM 50-SB from McIntyre Group Ltd.). The sulfoamphoterics may be utilized instead of the carboxylate amphoterics in some embodiments since the sulfonate group will remain ionized at much lower pH values.

Nonionic Surfactants. Exemplary nonionic surfactants include, but are not limited to, alkyl glucosides, alkyl polyglucosides, polyhydroxy fatty acid amides, sucrose esters, esters of fatty acids and polyhydric alcohols, fatty acid alkanolamides, ethoxylated fatty acids, ethoxylated aliphatic acids, ethoxylated fatty alcohols (e.g., octyl phenoxy polyethoxyethanol available under the trade name TRITON X-100 and nonyl phenoxy poly(ethyleneoxy) ethanol available under the trade name NONIDET P-40, both from Sigma, St. Louis, Mo.), ethoxylated and/or propoxylated aliphatic alcohols (e.g., that available under the trade name Brij from ICI), ethoxylated glycerides, ethoxylated/propoxylated block copolymers such as the Pluronic and Tetronic surfactants available from BASF, ethoxylated cyclic ether adducts, ethoxylated amide and imidazoline adducts, ethoxylated amine adducts, ethoxylated mercaptan adducts, ethoxylated condensates with alkyl phenols, ethoxylated nitrogen-based hydrophobes, ethoxylated polyoxypropylenes, polymeric silicones, fluorinated surfactants (e.g., those available under the trade names FLUORAD-FS 300 from 3M Company, St. Paul, Minn., and ZONYL from Dupont de Nemours Co., Wilmington, Del.), and polymerizable (reactive) surfactants (e.g., SAM 211 (alkylene polyalkoxy sulfate) surfactant available under the trade name MAZON from PPG Industries, Inc., Pittsburgh, Pa.). In some embodiments, the nonionic surfactants useful in the compositions can be selected from the group consisting of Poloxamers such as PLURONIC from BASF, sorbitan fatty acid esters like TWEEN, and mixtures thereof.

Disclosed compositions can also include other optional components. One such optional component includes antimicrobial components. Cationic quaternary ammonium salts (some of which are antimicrobial agents) including, but are not limited to cetyl pyridinium chloride, cetrimonium bromide (CTAB), behentrimonium chloride, bis-biguanides include chlorhexidine salts and polymeric guanides such as polyhexamethylenebiguanide (PHMB), benzethonium chloride, chlorhexidine salts such as chlorhexidine gluconate, octenidine salts such as octenidine dihydrochloride, stearalkonium chloride etc. and mixtures thereof can be used. The antimicrobials, if present can generally be present from 0.01-1 wt % based on the total weight of the composition. Non-ionic antimicrobials such as triclosan can also be used. Cationic compounds can be used in relatively small concentrations, as long as the stability of the composition is not compromised.

Amine compounds can also optionally be added to disclosed compositions. Amine compounds may be added in order to bind to the acrylate polymer, i.e. to help with neutralization of the polymer while also interacting with the surface of the spores. These can include, for example ethoxylated amines such as Jeffamines, and peg 8 oleyl amine.

Humectants can also optionally be added to disclosed compositions. Suitable humectants may include for example glycerin, propylene glycol, sorbitol, polypropylene glycol, polyethylene glycol, and combinations thereof.

Skin conditioning agents including emollients and polymers can also optionally be added to disclosed compositions. Useful skin conditioning agents such as mono-, di- and tri-glycerides, castor oil, allantoin, lanolin and its derivatives, cetyl alcohol and cationic polymers could be utilized for example. Emollients may be selected from those in U.S. Pat. No. 5,951,993 which is incorporated herein by reference, for example.

Thickeners can also optionally be added to disclosed compositions. In some embodiments, the thickeners could be organic thickeners. Suitable organic thickeners can include for example guar gum, hydroxyethyl cellulose, hydroxyl propyl cellulose, hydroxybutyl cellulose, hydroxypropyl methyl cellulose, polyvinylpyrrolidinone, as well as those disclosed in U.S. Pat. No. 8,062,649, incorporated herein by reference, which are used in the amount typically ranging from 0.1-2 wt % based on the total weight of the composition. Inorganic thickeners such as hydrated silica may be used in the amount of about 0.5-10 wt % or greater based on the total weigh of the composition.

Abrasive or mechanical exfoliating agents could also optionally be included in disclosed compositions. In some embodiments abrasive or exfoliating materials could include water insoluble abrasives such as phosphates, carbonates, silicates, hydrated silica, hydrated alumina, bentonite, as well as polymeric beads such a poly methyl methacrylate (PMMA), polystyrene, and polyolefin beads and particulates and the like as well as mixtures thereof. In some cases, other mild exfoliating agents could optionally be used in disclosed compositions for mechanically removing spores. Illustrative exfoliating agents could include arrowroot powder or walnut powder for example.

Also disclosed herein are methods of dislodging spores from a surface, methods of removing spores from a surface, or combinations thereof. Disclosed methods (and compositions) can be utilized on virtually any surface, including for example skin, medical equipment, surfaces in a medical environment, or any combinations thereof. In some embodiments, disclosed methods and compositions can be utilized on skin of patients, health care workers, other individuals, or any combination thereof. Disclosed methods can be utilized with various compositions, including those disclosed herein.

Some methods disclosed herein are methods of dislodging spores from a surface, or methods of removing spores from a surface. Illustrative examples of such methods can include steps of contacting the surface with a composition and in some embodiments subjecting the surface to mechanical action. The surface on which the spores are located and are to be dislodged can be contacted with a composition by applying or bringing the composition to the surface, by bringing the surface into contact with the composition, or by combinations thereof. More specifically, the composition and the surface can be brought into contact by spraying the composition onto the surface, by dispensing the composition onto the surface, by dipping the surface into the composition, by pouring the composition onto the surface, or by any combination thereof. In some embodiments, the step of contacting the surface with the composition can include contacting the surface with an article that has been previously contacted with the composition. For example, an article could be contacted with or treated with the composition and then that treated article could be contacted with the surface. Illustrative articles that could be treated with a composition can include, for example, wipes, sponges, or any combination thereof.

Some disclosed methods include a step of subjecting the surface contacted with the composition to mechanical action. Virtually any type of mechanical action could be utilized in disclosed methods. Illustrative types of mechanical action can include, for example, rubbing the surface with some article (for example an article treated with the composition, or an article not treated with the composition), moving or scraping an article across the surface, moving a surface contacted with the composition across another surface contacted with the composition, or any combination thereof. In some embodiments, mechanical action can include rubbing, wiping, scraping, or scouring the surface with the article treated with the composition. In some embodiments, mechanical action can include moving a first surface contacted with the composition across or over a second surface contacted with the composition. A specific example of such an embodiment can include rubbing two hands contacted with the composition together.

The step of subjecting the surface to mechanical action can occur for any amount of time. In some embodiments, the surface can be subjected to mechanical action for not less than 5 seconds, not less than 10 seconds, or not less than 20 seconds. In some embodiments, the surface can be subjected to mechanical action for not greater than 2 minutes, or not greater than 1 minute, for example.

In some embodiments, the steps of contacting the surface with a composition and subjecting the surface in contact with the composition to mechanical action can occur with at least some overlap. For example, in some embodiments, while at least some of the composition is being contacted with the surface, mechanical action can begin. Specifically, for example, while a hand, or hands, is being dipped into the composition (or even soaked in the composition), the hands can be rubbed together. Either (or both) of the steps of contacting the surface with the composition or subjecting the surface to mechanical action can be repeated more than once in some embodiments.

In some embodiments, the steps of contacting the composition with the surface and subjecting the surface to mechanical action can cause the copolymer particles to become associated with spores on the surface. It is thought, but not relied upon that the copolymer particles become associated with the outer surface of the spore. For example, it may be that the copolymer articles become adhered to the outer surface of the spores. Once the copolymer particles are associated with the spores the spores may be more easily removed from the surface then if they were not associated with the copolymer particles. In some embodiments, disclosed methods of dislodging spores can also include a step (or steps) of removing the dislodged spores from the surface, removing at least a portion of the applied composition, or a combination thereof.

It is thought, but not relied upon that the at least one low Tg component of the copolymer particles assists the copolymer particle with adhering to the spores and the at least one high Tg component of the copolymer particles assists the composition in removing the spore from the surface. Excess amounts of the at least one low Tg component or insufficient amounts of the at least one high Tg component may make it more difficult for the spores to be removed from the surface even though they are associated with the copolymer particles. Similarly, insufficient amounts of the at least one low Tg component or excess amounts of the at least one high Tg component may make it more difficult for the copolymer particle to adhere to the spores. The ratio of the at least one low Tg component to the at least one high Tg component may therefore be important to provide both adherence to the spore and removal of the spore from the surface. Disclosed compositions should allow for preferential bonding to the surface of the spore rather than to the surface on which the spore is located. In addition, disclosed compositions should weaken the interaction of the spores to the surface.

EXAMPLES

Objects and advantages are further illustrated by the following examples, but the particular materials and amounts thereof recited in these examples, as well as other conditions and details, should not be construed to unduly limit this disclosure.

Table 1 describes the list of reagents utilized herein.

TABLE 1

| Component | Supplier | Chemical Composition |
|---|---|---|
| Commercially Available Polymers | | |
| Aculyn 44 | Dow Personal Care, Midland MI | PEG-150/Decyl alcohol/SMDI (saturated methylenediphenyldiisocyanate) |
| Aculyn 46 | Dow Personal Care, Midland MI | PEG-150/Decyl alcohol/SMDI (saturated methylenediphenyldiisocyanate) |
| Amphomer | AkzoNobel, Amsterdam, Netherlands | octylacrylamide/butylaminoethyl methacrylate (Tg 33° C.)/acrylates |
| Avalure AC 120 | Lubrizol Advanced Material, Wickliffe OH | Ethyl acrylate (Tg −24° C.)/methyl methacrylate (Tg 105° C.)/acrylic acid (Tg 105° C.) |
| Avalure AC 210 | Lubrizol Advanced Material, Wickliffe OH | Ethyl acrylate (Tg −24° C.)/methyl methacrylate (Tg 105° C.)/acrylic acid (Tg 105° C.) |
| Avalure AC 315 | Lubrizol Advanced Material, Wickliffe OH | Ethyl acrylate (Tg −24° C.)/methyl methacrylate (Tg 105° C.)/acrylic acid (Tg 105° C.) |
| Avalure UR 450 | Lubrizol Advanced Material, Wickliffe OH | PPG-17/IPDI/DMPA |
| Balance 0/55 | AkzoNobel, Amsterdam, Netherlands | acrylates copolymer |
| Balance CR | AkzoNobel, Amsterdam, Netherlands | Butyl acrylate (Tg −54° C.)/methyl methacrylate (Tg 105° C.)/methacrylic acid (Tg 228° C.) |
| Dermacryl C | AkzoNobel, Amsterdam, Netherlands | 2-ethylhexyl acrylate (Tg −50° C.)/methyl methacrylate (Tg 105° C.) |
| Eudragit RLPO | Evonik Industries, Essen, Germany | ethyl acrylate (Tg −24° C.)/methyl methacrylate (Tg 105° C.)/methacrylic acid (Tg 228° C.) ester/quat ammonia group |
| Gantrez ES-225 | Ashland, Covington, KY (bought International Specialty Products) | ethyl ester of poly(methylvinylether (Tg −31° C.)/maleic acid) copolymer |
| Gantrez S-97 | Ashland, Covington, KY (bought International Specialty Products) | Methylvinylether (Tg −31° C.)/maleic acid copolymer |
| Polectron 430 | Ashland, Covington, KY (bought International Specialty Products) | 30% PVP (Tg 54° C.) and 70% styrene (Tg 100° C.) |
| PVP K-30 | Ashland, Covington, KY (bought International Specialty Products) | Polyvinylpyrrolidone |
| PVP/VA S-630 | Ashland, Covington, KY (bought International | vinyl acetate (Tg 30° C.)/vinyl pyrrolidone (Tg 54° C.) |

TABLE 1-continued

| Component | Supplier | Chemical Composition |
|---|---|---|
| Structure Plus | Specialty Products) AkzoNobel, Amsterdam, Netherlands | acrylates/aminoacrylates/C10-30 alkyl PEG-20 itaconate copolymer |

Prepared Polymers and Component Monomers

| Component | Supplier | Chemical Composition |
|---|---|---|
| 2-EHA/MMA | 3M MRD, St. Paul, MN | 2-ethylhexyl acrylate (Tg −50° C.)/methyl methacrylate (Tg 105° C.) |
| 2-EHA/MMA/AA | 3M MRD, St. Paul, MN | 2-ethylhexyl acrylate (Tg −50° C.)/methyl methacrylate (Tg 105° C.)/acrylic acid (Tg 105° C.) |
| 2-EHA/MMA/QMA | 3M MRD, St. Paul, MN | 2-ethylhexyl acrylate (Tg −50° C.)/methyl methacrylate (Tg 105° C.)/Quaternary methacrylate (Tg 100° C.) |
| IOA/BA/HEA | 3M MRD, St. Paul, MN | Isooctylacrylate (Tg −58)/butyl acrylate (Tg −54)/hydroxyethyl acrylate (Tg 15) |
| IOA/BA/HEMA/ NMA | 3M MRD, St. Paul, MN | Isooctylacrylate (Tg −58° C.)/butyl acrylate (Tg −54° C.)/hydroxyethylmethacrylate (Tg 55° C.)/N-methyl acrylamide (Tg 89° C.) |
| 2-EHA | Sigma-Aldrich Corp. St. Louis, MO | 2-ethylhexyl acrylate monomer |
| MMA | Sigma-Aldrich Corp. St. Louis, MO | Methyl methacrylate monomer |
| IOA | Sigma-Aldrich Corp. St. Louis, MO | Isooctylacrylate monomer |
| BA | Sigma-Aldrich Corp. St. Louis, MO | Butyl acrylate monomer |
| HEA | Sigma-Aldrich Corp. St. Louis, MO | Hydroxyethyl acrylate monomer |
| HEMA | Sigma-Aldrich Corp. St. Louis, MO | Hydroxyethylmethacrylate monomer |
| NMA | Ark Pharm, Inc Libertyville, IL | N-methyl acrylamide |
| AA | Sigma-Aldrich Corp. St. Louis, MO | Acrylic acid |
| QMA | Sigma-Aldrich Corp. St. Louis, MO | Quaternary ammonium salt of dimethylaminoethyl methacrylate |

Anionic Surfactants

| Component | Supplier | Chemical Composition |
|---|---|---|
| Complemix 100 | Cytec Industries, Woodland Park, NJ | dioctyl sodium sulfosuccinate |
| Polystep B-11 | Stepan Company, Northfield, IL | Ammonium lauryl ether sulfate (4 EO) |
| Polystep B-22 | Stepan Company, Northfield, IL | Ammonium lauryl ether sulfate (12 EO) |
| Rhodacal DS-10 | Solvay, Brussels, Belgium (bought Rhodia) | sodium dodecylbenzene sulfonate |
| Stepan Mild RM-1 | Stepan Company, Northfield, IL | Sodium stearyl phthalamate |
| Stepan Mild SL3 | Stepan Company, Northfield, IL | Disodium laureth sulfosuccinate |
| Stepan Steol CA-460 | Stepan Company, Northfield, IL | Ammonium laureth sulfate (3 EO) |
| SDS | Sigma-Aldrich Corp. St. Louis, MO | sodium dodecyl sulfate |

Nonionic Surfactants

| Component | Supplier | Chemical Composition |
|---|---|---|
| Igepal CO-887 | Stepan Company, Northfield, IL | nonyl phenol ethoxylate |
| Triton X-100 | Dow Chemical Company, Midland, MI | octylphenyl ethoxylate |
| Tween 20 | Sigma-Aldrich Corp. St. Louis, MO | polyoxyethylenesorbitan monolaurate |
| Tween 80 | Sigma-Aldrich Corp. St. Louis, MO | polyoxyethylenesorbitan monooleate |

Zwitterionic Surfactants

| Component | Supplier | Chemical Composition |
|---|---|---|
| CAHS | Solvay, Brussels, Belgium (bought Rhodia) | Cocamidopropyl hydroxy sultaine (sold as 45% active Mackam 45 SB) |
| CAPB | Solvay, Brussels, Belgium (bought Rhodia) | cocamidopropyl betaine (35% active Mackam CB-35) |

TABLE 1-continued

| Component | Supplier | Chemical Composition |
|---|---|---|
| Charge Neutralizers or Antimicrobials | | |
| | Sigma-Aldrich Corp. St. Louis, MO | Cetrimonium Bromide |
| CPC | Sigma-Aldrich Corp. St. Louis, MO | Cetylpyridinium chloride |
| PHMB | Lonza, Basel, Switzerland | polyhexamethylene biguanide (sold as 20% Cosmocil CQ) |
| Particle Additives | | |
| Floraspheres | FloraTech, Chandler, AZ | jojoba ester beads > 500 um |
| Gotalene 120 | DuPont Polymer Powders, Bulle, Switzerland | low density polyethylene beads < 630 μm |
| Jojoba Beads | Essential Wholesale, Portland, OR | jojoba wax beads 250-460 um |
| Unispheres | Induchem, Volketswil, Switzerland | mannitol and cellulose beads > 500 μm |
| | Alfa Aesar, Ward Hill, MA | zinc oxide 44 μm |
| Thickeners | | |
| Carbopol 940 | Lubrizol Advanced Material, Wickliffe OH | carbomer |
| Carbopol Ultrez 10 | Lubrizol Advanced Material, Wickliffe OH | carbomer |
| Pemulen TR-2 | Lubrizol Advanced Material, Wickliffe OH | Acrylates/C10-30 alkyl acrylate crosspolymer |
| Other Chemicals | | |
| | Spectrum Chemicals, New Brunswick, NJ | amino methyl propanol |
| | Sigma-Aldrich Corp. St. Louis, MO | Ammonium persulfate |
| D/E Neutralizing Broth | Becton Dickinson, Franklin Lakes, NJ | Dey/Engley Neutralizing Broth |
| 200 Proof Ethanol | Columbus Chemical Industries, Columbus, WI | ethanol |
| HCl | J.T. Baker of Avantor Preformance Materials, Center Valley, PA | hydrochloric acid |
| KH2PO4 | Sigma-Aldrich Corp. St. Louis, MO | potassium phosphate monobasic |
| Propylene Glycol | EMD Millipore, Billerica, MA | 1,2-Propanediol |
| NaOH | EM Science of EMD Millipore, Billerica, MA | Sodium Hydroxide |
| | Sigma-Aldrich Corp. St. Louis, MO | Sodium metabisulfate |
| Na2HPO4 | Sigma-Aldrich Corp. St. Louis, MO | sodium phosphate dibasic |
| | Essential Wholesale, Portland, OR | stearic acid |
| TEA | Sigma-Aldrich Corp. St. Louis, MO | Triethanolamine |

Table 2 gives the glass transition temperatures for monomers utilized herein.

TABLE 2

| Chemical Name | Glass Transition Temperature of homopolymer (° C.) |
|---|---|
| 2-ethylhexyl acrylate EHA | −50 |
| Methyl methacrylate MMA | 105 |
| Methyl vinyl ether MVE | −31 |
| Vinyl acetate VA | 30 |
| Vinyl pyrrolidone VP | 54 |
| Butyl acrylate BA | −54 |
| Acrylic acid AA | 105 |
| Isooctylacrylate IOA | −58 |
| Hydroxyethylmethacrylate HEMA | 55 |
| Hydroxyethyl acrylate HEA | 15 |
| Lauryl acrylate LA | 15 |
| QMA | 100 |
| Styrene | 100 |
| Ethyl acrylate EA | −24 |
| Methacrylic acid MAA | 228 |
| N-methyl acrylamide | 89 |
| Butylaminoethyl methacrylate | 33 |

Example 1: Preparation of formulations

All of the formulations that were tested for their ability to remove spores from Vitro Skin were constructed in the same fashion.

First the correct amount of polymer was added to a vial, then water was added. If necessary additional components such as surfactants, beads etc. were added. The solution was mixed well and the pH was measured. The pH was adjusted, if necessary, with either sodium hydroxide or hydrochloric acid to a final pH around 6.5-7. Finally ethanol was added so that the solution was approximately 70% by weight ethanol and the solution was mixed again.

Example 2: General Description of In-Vitro Experiment Designed to Evaluate Ability of Test Formulations to Remove Spores from Skin Like Surfaces The in-vitro method was designed to evaluate the removal of microbes from skin using a synthetic skin material from the cosmetic industry, Vitro-skin from IMS Inc., Portland Me. This method enables rapid screening of formulations for their propensity to promote release of microbes from skin and may be predictive of in-vivo activity.

Materials

The following materials were utilized. *C. sporogenes* spores ATCC 3584~$1.0 \times 10^8$ CFU/ml; Triton-X 100 sampling buffer (pH 7.4) Filter Sterilized: 0.4 g KH2PO4, 10.1 g Na2HPO4, 1 g Triton-X 100, and 1 L dH2O; D/E neutralizing broth; Fingers from disposable polyethylene gloves (VWR 32915-268); Sterile dH2O (WFI quality water); 3M AC Petrifilm; and 5 ml Falcon tubes; 1.5 ml EPI Centrifuge tubes; Petri Dishes; Vitro-Skin IMS Inc.; and double-sided tape.

The method included the following. Punched-out specified number of Vitro-Skin samples using the ¾" punch. Attached punch-out Vitro-Skin samples to a Petri-dish or any other sterile flat surface using double-sided tape. Contaminated the Vitro-Skin samples accordingly with 10 μl of spores/spore prep (~$1 \times 10^6$ CFU/Sample). Used the pipette tip to spread spores over the surface and used a new pipette tip for each sample. Allowed the samples to dry (~40 minutes). Placed three samples directly into separate finger bags containing 3 ml of Triton X-100 sampling solution or D/E neutralizing broth if the sample to be tested contained an antimicrobial. Used the "Finger bag collection method" below for each of the three recovery controls.

The Finger bag collection method was carried out as follows. First, a finger bag was cut from disposable gloves (VWR International disposable polyethylene gloves, size large). Filled the finger bag with 3 ml of sampling solution. Placed contaminated Vitro-Skin sample into the finger bag containing sampling solution. Massaged finger bag for 1 minute using thumb and index finger. Removed aliquot of fluid from the finger bag and place into an appropriately labeled 1.5 ml centrifuge tube.

For the experimental samples, contaminated Vitro-Skin samples were placed into a finger bag containing 3 ml of appropriate test solution. Massage in finger bag for 20 seconds. Removed the Vitro-Skin sample from the finger bag and place into a new finger bag containing 3 ml of sampling solution (Triton X-100 glove juice buffer or D/E neutralizing broth). Collected sample by using the finger bag collection method noted above. Repeat "Placed contaminated vitro-skin sample . . . " to "Collected sample . . . " for each of the test solutions. For best statistical data each test solution was repeated 3 times. Heat treated appropriately labeled 1.5 ml centrifuge tubes containing aliquots of solution for 20 min at 80° C. Serially diluted samples in butterfield's buffer and plate $10^{-1}$ to $10^{-4}$ dilution on AC Petrifilm. Heat shocked, diluted, and plated spore stock day of experiment. Incubated Petrifilm in an anaerobic chamber at 37 C for 20-24 hours. Counted plates and analyzed data.

Example 3: Effect of pH and Concentration on Dermacryl C Formulations

The formulations in Table 3 were prepared according to Example 1 above and tested according to Example 2 above.

TABLE 3

|  | 3-1 | 3-2 | 3-3 | 3-4 | 3-5 | 3-6 |
|---|---|---|---|---|---|---|
| CAHS | 0 | 0 | 0.5 | 0.5 | 0.5 | 0.5 |
| CPC | 0 | 0 | 0.2 | 0.2 | 0.2 | 0.2 |
| Dermacryl C | 0 | 0 | 0.25 | 1 | 0.25 | 1 |
| 200 Proof Ethanol | 0 | 70 | 70 | 70 | 70 | 70 |
| Water | 100 | 30 | 29.05 | 28.3 | 29.05 | 28.3 |
| pH |  | 8.5 | 6.8 | 6.8 | 8.5 | 8.5 |
| Log Reduction | 1.02 | 0.49 | 1.13 | 1.83 | 0.99 | 0.87 |
| Standard Deviation | 0.2 | 0.13 | 0.28 | 0.29 | 0.12 | 0.32 |

The data in Table 3 suggests formulations including Dermacryl C remove more spores at pH 6.8 then at pH 8.5. Increased concentrations of Dermacryl C in formulations increase removal when pH is 6.8. In this example and all following examples, 70% ethanol and water were used as controls for all formulations. Spore reduction is very poor in 70% ethanol but better in water. The goal here is to formulate in 70% ethanol such that the performance at least that of a water control. Formulations where the spore removal is similar to water (log reduction within 0.2 logs of water) or exceeds that of water would be preferred. Formulations that are closer to ethanol controls (within 0.2 logs of ethanol) would not be preferred. Formulations in between would be acceptable but would be most preferable with results close to or exceeding water controls.

Example 4: Effect of pH and Concentration on Balance 0/55 Formulations

The formulations in Table 4 were prepared according to Example 1 above and tested according to Example 2 above.

TABLE 4

|  | 4-1 | 4-2 | 4-3 | 4-4 | 4-5 | 4-6 | 4-7 |
|---|---|---|---|---|---|---|---|
| CAHS | 0 | 0 | 0 | 0.5 | 0.5 | 0.5 | 0.5 |
| CPC | 0 | 0 | 0 | 0.2 | 0.2 | 0.2 | 0.2 |
| Balance 0/55 | 0 | 0 | 0.5 | 0.5 | 2 | 0.5 | 2 |
| 200 Proof Ethanol | 0 | 70 | 70 | 70 | 70 | 70 | 70 |
| Water | 100 | 30 | 29.5 | 28.8 | 27.3 | 28.8 | 27.3 |
| pH |  | 8.5 | 8.5 | 6.8 | 6.8 | 8.5 | 8.5 |
| Log Reduction | 1.02 | 0.49 | 0.32 | 0.73 | 0.74 | 1.02 | 1.15 |
| Standard Deviation | 0.20 | 0.13 | 0.07 | 0.08 | 0.12 | 0.27 | 0.30 |

The data in Table 4 suggests that increasing pH increases the efficacy of Balance 0/55 to remove spores. Concentration of Balance 0/55 does not statistically effect removal of spores.

Example 5: Polymers were Varied in Formulation and the Effect on Spore Removal was Studied The formulations in Table 5 were prepared according to Example 1 and tested for their spore removal efficacy according to Example 2 above.

TABLE 5

| | 5a-1 | 5a-2 | 5a-3 | 5a-4* | 5a-5* | 5a-6 | 5a-7 | 5a-8 | 5a-9 | 5a-10 | 5a-11 |
|---|---|---|---|---|---|---|---|---|---|---|---|
| CAHS | 0 | 0 | 1 | 1 | 1 | 1 | 1 | 1 | 1 | 1 | 1 |
| CPC | 0 | 0 | 0.2 | 0.2 | 0.2 | 0.2 | 0.2 | 0.2 | 0.2 | 0.2 | 0.2 |
| Dermacryl C | 0 | 0 | 0 | 1 | 1 | 0 | 0 | 0 | 0 | 0 | 0 |
| Aculyn 44 | 0 | 0 | 0 | 0 | 0 | 2 | 0 | 0 | 0 | 0 | 0 |
| Aculyn 46 | 0 | 0 | 0 | 0 | 0 | 0 | 2 | 0 | 0 | 0 | 0 |
| PVP K-30 | 0 | 0 | 0 | 0 | 0 | 0 | 0 | 2 | 0 | 0 | 0 |
| PVP/VA S-630 | 0 | 0 | 0 | 0 | 0 | 0 | 0 | 0 | 2 | 0 | 0 |
| Gantrez ES-225 | 0 | 0 | 0 | 0 | 0 | 0 | 0 | 0 | 0 | 2 | 0 |
| Gantrez S-97 | 0 | 0 | 0 | 0 | 0 | 0 | 0 | 0 | 0 | 0 | 2 |
| 200 Proof Ethanol | 0 | 70 | 70 | 70 | 70 | 70 | 70 | 70 | 70 | 70 | 70 |
| Water | 100 | 30 | 28.8 | 27.8 | 27.8 | 26.8 | 26.8 | 26.8 | 26.8 | 26.8 | 26.8 |
| Log Reduction | 1.54 | 0.22 | 0.57 | 1.73 | 1.50 | 0.54 | 0.53 | 0.53 | 0.49 | 0.28 | 0.10 |
| Standard Deviation | 0.23 | 0.03 | 0.11 | 0.41 | 0.09 | 0.05 | 0.15 | 0.19 | 0.11 | 0.04 | 0.06 |

*5a-4 was made previous to the testing day and 5a-5 was made on the testing day.

| | 5b-1 | 5b-2 | 5b-3 | 5b-4 | 5b-5 | 5b-6 | 5b-7 |
|---|---|---|---|---|---|---|---|
| CAHS | 0 | 0 | 1 | 1 | 1 | 1 | 1 |
| CPC | 0 | 0 | 0.2 | 0.2 | 0.2 | 0.2 | 0.2 |
| Polectron 430 | 0 | 0 | 2 | 0 | 0 | 0 | 0 |
| Avalure UR 450 | 0 | 0 | 0 | 2 | 0 | 0 | 0 |
| Avalure AC 315 | 0 | 0 | 0 | 0 | 2 | 0 | 0 |
| Avalure AC 210 | 0 | 0 | 0 | 0 | 0 | 2 | 0 |
| Avalure AC 120 | 0 | 0 | 0 | 0 | 0 | 0 | 2 |
| 200 Proof Ethanol | 0 | 70 | 70 | 70 | 70 | 70 | 70 |
| Water | 100 | 30 | 26.8 | 26.8 | 26.8 | 26.8 | 26.8 |
| Log Reduction | 1.00 | 0.32 | 0.23 | 0.76 | 0.60 | 1.01 | 0.88 |
| Standard Deviation | 0.15 | 0.04 | 0.24 | 0.09 | 0.34 | 0.28 | 0.12 |

| | 5c-1 | 5c-2 | 5c-3 | 5c-4 | 5c-5 | 5c-6 | 5c-7 | 5c-8 | 5c-9 |
|---|---|---|---|---|---|---|---|---|---|
| CAHS | 0 | 0 | 0.5 | 0.5 | 0.5 | 0.5 | 0.5 | 0.5 | 0.5 |
| CPC | 0 | 0 | 0 | 0.2 | 0.2 | 0.2 | 0.2 | 0.2 | 0.2 |
| PHMB | 0 | 0 | 0.2 | 0 | 0 | 0 | 0 | 0 | 0 |
| Dermacryl C | 0 | 0 | 0 | 0 | 0.25 | 0 | 0 | 0 | 0 |
| Structure Plus | 0 | 0 | 0 | 0 | 0 | 0.5 | 0 | 0 | 0 |
| Balance 0/55 | 0 | 0 | 0 | 0 | 0 | 0 | 0.5 | 0 | 0 |
| Amphomer | 0 | 0 | 0 | 0 | 0 | 0 | 0 | 0.5 | 0 |
| Eudrajit RLPO | 0 | 0 | 0 | 0 | 0 | 0 | 0 | 0 | 0.5 |
| 200 Proof Ethanol | 0 | 70 | 70 | 70 | 70 | 70 | 70 | 70 | 70 |
| Water | 100 | 30 | 29.3 | 29.3 | 29.05 | 28.8 | 28.8 | 28.8 | 28.8 |
| pH | | 8.5 | 8.5 | 8.5 | 8.6 | 8.6 | 8.6 | 8.5 | 8.6 |
| Log Reduction | 1.15 | 0.52 | 0.51 | 0.62 | 1.17 | 0.86 | 1.04 | 0.59 | 0.51 |
| Standard Deviation | 0.13 | 0.05 | 0.09 | 0.11 | 0.19 | 0.20 | 0.20 | 0.05 | 0.08 |

The results in Table 5 indicate other film forming polymers without the low Tg acrylate monomer do not remove spores as well as Dermacryl C, Balance and Avalure 210 formulations.

Example 6: Effect of Surfactants on Spore Removal

Several components including anionic surfactants that can be used to stabilize the emulsion can potentially play a role in spore removal. To understand this, anionic surfactants such as sodium lauryl ether sulfate were added to CPC and Mackam and formulations were created in the absence of film former such as Dermacryl C. The formulations shown in Table 6 below were prepared according to Example 1 and were tested according to Example 2 above.

TABLE 6

| | 6-1 | 6-2 | 6-3 | 6-4 | 6-5 | 6-6 | 6-7 |
|---|---|---|---|---|---|---|---|
| CAHS | 0.0 | 0.0 | 1.0 | 1.0 | 1.0 | 1.0 | 1.0 |
| CPC | 0.0 | 0.0 | 0.2 | 0.2 | 0.2 | 0.2 | 0.2 |
| Stepan Mild RM-1 | 0.0 | 0.0 | 2.0 | 0.0 | 0.0 | 0.0 | 0.0 |
| Stepan Mild SL3 | 0.0 | 0.0 | 0.0 | 2.0 | 0.0 | 0.0 | 0.0 |
| Stepan Steol CA-460 | 0.0 | 0.0 | 0.0 | 0.0 | 2.0 | 0.0 | 0.0 |
| Polystep B-22 | 0.0 | 0.0 | 0.0 | 0.0 | 0.0 | 2.0 | 0.0 |
| Polystep B-11 | 0.0 | 0.0 | 0.0 | 0.0 | 0.0 | 0.0 | 2.0 |
| 200 Proof Ethanol | 0.0 | 70.0 | 70.0 | 70.0 | 70.0 | 70.0 | 70.0 |
| Water | 100.0 | 30.0 | 26.8 | 26.8 | 26.8 | 26.8 | 26.8 |
| Log Reduction | 0.90 | 0.18 | 0.35 | 0.12 | 0.30 | 0.29 | 0.40 |
| Standard Deviation | 0.19 | 0.12 | 0.09 | 0.14 | 0.12 | 0.07 | 0.05 |

The data shown in Table 6 indicates that the surfactants by themselves are not responsible for the improved efficiency of spore removal in high alcohol mediums.

Example 7: Effect of Beads on Spore Removal

Formulations according to Table 7 were made according to Example 1, with the note that Dermacryl solutions were made first and then the beads added to the solution. The formulations were then tested according to Example 2 above.

TABLE 7

|  | 7a-1 | 7a-2 | 7a-3 | 7a-4 | 7a-5 | 7a-6 |
|---|---|---|---|---|---|---|
| CAHS | 0 | 0 | 1 | 1 | 1 | 1 |
| Cetrimonium Bromide | 0 | 0 | 0.25 | 0.25 | 0.25 | 0.25 |
| Dermacryl C | 0 | 0 | 4 | 4 | 4 | 4 |
| 1.0N NaOH | 0 | 0 | 0.024 | 0.088 | 0.03 | 0.018 |
| 200 Proof Ethanol | 0 | 70 | 70 | 70 | 70 | 70 |
| Water | 100 | 30 | 24.726 | 23.662 | 23.72 | 23.732 |
| Jojoba Beads | 0 | 0 | 0 | 1 | 0 | 0 |
| Gotalene 120 | 0 | 0 | 0 | 0 | 1 | 0 |
| Zinc Oxide | 0 | 0 | 0 | 0 | 0 | 1 |
| pH |  |  | 7.14 | 7.14 | 7.15 | 7.16 |
| Log Reduction | 1.12 | 0.42 | 1.71 | 1.75 | 1.45 | 2.15 |
| Standard Deviation | 0.37 | 0.08 | 0.41 | 0.15 | 0.28 | 0.38 |

|  | 7b-1 | 7b-2 | 7b-3 | 7b-4 | 7b-5 |
|---|---|---|---|---|---|
| CAHS | 0 | 0 | 1.00 | 0.989 | 0.989 |
| Cetrimonium Bromide | 0 | 0 | 0.25 | 0.247 | 0.247 |

TABLE 7-continued

| Dermacryl C | 0 | 0 | 2.000 | 1.978 | 1.978 |
|---|---|---|---|---|---|
| 1.0N NaOH | 0 | 0 | 0.024 | 0.024 | 0.024 |
| 200 Proof Ethanol | 0 | 70.000 | 70.000 | 69.239 | 69.239 |
| Water | 100.000 | 30.000 | 26.726 | 26.567 | 26.567 |
| Unispheres | 0 | 0 | 0 | 0.955 | 0 |
| Floraspheres | 0 | 0 | 0 | 0 | 0.955 |
| pH |  |  | 7.18 | 7.18 | 7.18 |
| Log Reduction | 1.16 | 0.27 | 1.12 | 0.69 | 1.84 |
| Standard Deviation | 0.24 | 0.06 | 0.23 | 0.26 | 0.20 |

The data shown in Table 7 shows that the use of beads, such as Floraspheres, may increase removal of spores from skin like surfaces.

Example 8: Using Balance and Varying Excipients in Solution

The formulations in Table 8 were prepared according to Example 1 above and tested according to Example 2 above.

TABLE 8

|  | 8-1 | 8-2 | 8-3 | 8-4 | 8-5 | 8-6 |
|---|---|---|---|---|---|---|
| Dermacryl C | 0.000 | 0.000 | 2.000 | 2.000 | 0.000 | 0.000 |
| Balance CR | 0.000 | 0.000 | 0.000 | 0.000 | 2.000 | 0.000 |
| Balance O/55 | 0.000 | 0.000 | 0.000 | 0.000 | 0.000 | 2.000 |
| CAHS | 0.000 | 0.000 | 0.000 | 1.000 | 1.000 | 1.000 |
| Cetrimonium Bromide | 0.000 | 0.000 | 0.000 | 0.250 | 0.250 | 0.250 |
| Tween 20 | 0.000 | 0.000 | 3.000 | 3.000 | 0.000 | 0.000 |
| 1.0N NaOH | 0.000 | 0.000 | 0.366 | 0.000 | 1.022 | 1.422 |
| 200 Proof Ethanol | 0.000 | 70.000 | 70.000 | 70.000 | 70.000 | 70.000 |
| Water | 100.000 | 30.000 | 24.634 | 23.75 | 25.728 | 25.328 |
| pH |  |  | 7.24 | 7.24 | 8.38 | 7.92 |
| Log Reduction | 1.42 | 0.31 | 0.5 | 1.42 | 0.32 | 0.47 |
| Standard Deviation | 0.23 | 0.07 | 0.02 | 0.34 | 0.07 | 0.18 |

Example 9: Comparative Example: Effect of Commonly Used Thickeners in 70% Alcohol Solutions on Spore Removal The formulations in Table 9 were prepared according to Example 1 above and tested according to Example 2 above.

TABLE 9

|  | 9-1 | 9-2 | 9-3 | 9-4 | 9-5 | 9-6 | 9-7 |
|---|---|---|---|---|---|---|---|
| Carbopol 940 | 0.000 | 0.000 | 0.000 | 0.000 | 0.251 | 0.000 | 0.000 |
| Carbopol Ultrez 10 | 0.000 | 0.000 | 0.000 | 0.000 | 0.000 | 0.247 | 0.000 |
| Pemulen TR-2 | 0.000 | 0.000 | 0.000 | 0.000 | 0.000 | 0.000 | 0.246 |
| Dermacryl C | 0.000 | 0.000 | 4.018 | 4.019 | 0.000 | 0.000 | 0.000 |
| CAHS | 0.000 | 0.000 | 0.000 | 2.214 | 0.000 | 0.000 | 0.000 |
| Cetrimonium Bromide | 0.000 | 0.000 | 0.000 | 0.249 | 0.000 | 0.000 | 0.000 |
| Amino Methyl Propanol | 0.000 | 0.000 | 0.000 | 0.000 | 0.131 | 0.217 | 0.117 |
| 1.0N HCl | 0.000 | 0.000 | 0.116 | 0.000 | 0.000 | 0.000 | 0.000 |
| 1.0N NaOH | 0.000 | 0.000 | 0.000 | 0.467 | 0.000 | 0.000 | 0.000 |
| 200 Proof Ethanol | 0.000 | 70.000 | 69.995 | 70.026 | 70.022 | 69.999 | 70.009 |
| Water | 100.000 | 30.000 | 25.908 | 23.066 | 29.636 | 29.563 | 29.601 |
| pH |  |  | 7.24 | 7.11 | 6.51 | 6.66 | 7.24 |
| Log Reduction | 1.26 | 0.43 | 0.96 | 1.06 | 0.19 | 0.28 | 0.18 |
| Standard Deviation | 0.25 | 0.09 | 0.19 | 0.17 | 0.14 | 0.06 | 0.05 |

The data in Table 9 shows that commonly used anionic acrylate thickeners do not show good spore removal as compared to the acrylate formulations described here.

Example 10: The Typical Synthesis of a Latex Comprising High Tg and Low Tg Component is Described Below Synthesis of 2-EHA/MMA, 75/25 Latex:

| Charge | Material | Function | Wt (g) |
|---|---|---|---|
| A | DI H2O | Solvent | 560 |
| B | Tween 80, 100% | Surfactant | 12 |
| C | Monomer Premix (see below) | monomers | 48 |

-continued

| Charge | Material | Function | Wt (g) |
|---|---|---|---|
| D | Ammonium persulfate | Initiator | 0.48 |
| E | Sodium metabisulfite | Initiator | 0.12 |
| F | 0.15% FeSO4•7H2O | Catalyst | 3 |
| G | Metered monomer premix 2-EHA/MMA, 75/25 Premix (made in excess of what is needed) | monomers | 192 g |
| H | 2-EHA | monomer | 262.5 |
| I | MMA | monomer | 87.5 |

Procedure: In a 500 ml glass jar, Charge H, 262.5 g of 2-EHA and Charge I, 87.5 g MMA were charged. The resulting homogeneous mixture was labeled as Premix. A 3 liter, 3 neck resin flask was charged with Charge A, 560 g of DI H2O and Charge B, 12 g of Tween 80 surfactant. The mixture was stirred at 230 rpm at 30° C. Charged C, D, E and F to the flask followed by another 60 g DI H2O. Metered in 192 g of premix at 1.6 g/min over 2 hr to control the exotherm. Reacted the resulting mixture at 55° C. for about 3 hrs. The reaction was run for another 2 hrs at 70° C. The resulting latex was cooled to RT. The latex was filtered through 2 layers of preweighed cheese cloth (Grade 50) before % solids were measured. The amount of coagulum was measured after removing H2O from the material collected on the cheese cloth. % coagulum is reported based on the total amount of latex.

The Samples shown in Table 10 below were prepared using this procedure.

TABLE 10

Acrylic Latex Comprising High Tg and Low Tg Monomers Stabilized with Various Surfactants

| Sample ID | Composition | Surfactant | Solids in water (%) | % Coagulation (based on total latex) |
|---|---|---|---|---|
| 157555-56 | 2-EHA/MMA 75/25 | 5% Tween 80 | 30.15 | 0.80 |
| 157555-53 | 2-EHA/AA 50/50 | 5% Tween 80 | 30.76 | 0.41 |
| 157555-52 | 2-EHA/AA 25/75 | 5% Tween 80 | 28.58 | 0.61 |
| 156265-32 | 2-EHA/MMA 75/25 | 3% Igepal CO-887 | 29.68 | 0.85 |
| 156265-8 | 2-EHA/MMA 54/44 | 3% Igepal CO-887 | 30.36 | 0.42 |
| 156265-28 | 2-EHA/MMA 25/75 | 3% Igepal CO-887 | 29.45 | 0.28 |
| 156265-30 | 2-EHA/MMA/AA 73/25/2 | 3% Rhodacal DS-10 | 29.97 | 0.32 |
| 156265-6 | 2-EHA/MMA/AA 56/42/2 | 3% Rhodacal DS-10 | 32.36 | 0.24 |
| 156265-22 | 2-EHA/MMA/AA 25/73/2 | 3% Rhodacal DS-10 | 29.99 | 0.25 |
| 157555-72 | 2-EHA/MMA/AA 70/22/8 | 3% DS-10 | 30.01 | 0.78 |
| 159177-102 | 2-EHA/MMA 75/25 | 3% DS-10 | 30.36 | 0.31 |

Formulation preparation: The acrylate polymers were added to water and mixed. The pH was adjusted with either sodium hydroxide or hydrochloric acid unless otherwise stated followed by the addition of 200 proof ethanol.

Example 11: Effect of EHA:MMA Ratio on Spore Removal

The formulations in Tables 11a and 11b were prepared according to Example 10 above and tested according to Example 2 above. The formulations in Table 11a were stabilized with Tween 80, those in Table 11b with Igepal CO-887.

TABLE 11a

| | 11a-1 | 11a-2 | 11a-3 | 11a-4 | 11a-5 |
|---|---|---|---|---|---|
| 2-EHA/MMA [75/25] 5% Tween 80 | 0.000 | 0.000 | 2.000 | 0.000 | 0.000 |
| 2-EHA/MMA [50/50] 5% Tween 80 | 0.000 | 0.000 | 0.000 | 2.000 | 0.000 |
| 2-EHA/MMA [25/75] 5% Tween 80 | 0.000 | 0.000 | 0.000 | 0.000 | 2.000 |
| 1.0N NaOH | 0.000 | 0.000 | 0.188 | 0.196 | 0.152 |
| 1.0N HCl | 0.000 | 0.000 | mix | mix | 0.000 |
| 200 Proof Ethanol | 0.000 | 70.000 | 70.000 | 70.000 | 70.000 |
| Water | 100.000 | 30.000 | 27.812 | 27.804 | 27.848 |
| pH | | | 6.77 | 7.17 | 6.78 |
| Log Reduction | 0.96 | 0.38 | 1.19 | 0.42 | 0.46 |
| Standard Deviation | 0.16 | 0.12 | 0.35 | 0.15 | 0.15 |

The data shows that the 75/25 EHA:MMA provided the best spore removal performance.

TABLE 11b

| | 11b-1 | 11b-2 | 11b-3 | 11b-4 | 11b-5 |
|---|---|---|---|---|---|
| 2-EHA/MMA [75/25] 3% Igepal CO-887 | 0.000 | 0.000 | 2.000 | 0.000 | 0.000 |
| 2-EHA/MMA [56/44] 3% Igepal CO-887 | 0.000 | 0.000 | 0.000 | 2.000 | 0.000 |
| 2-EHA/MMA [25/75] 3% Igepal CO-887 | 0.000 | 0.000 | 0.000 | 0.000 | 2.000 |
| 1.0N NaOH | 0.000 | 0.000 | 0.944 | 0.410 | 0.306 |
| 1.0N HCl | 0.000 | 0.000 | mix | mix | mix |
| 200 Proof Ethanol | 0.000 | 70.000 | 70.000 | 70.000 | 70.000 |
| Water | 100.000 | 30.000 | 27.812 | 27.804 | 27.848 |
| pH | | | 6.98 | 7.37 | 7.13 |
| Log Reduction | 1.42 | 0.22 | 0.90 | 1.12 | 0.48 |
| Standard Deviation | 0.06 | 0.13 | 0.28 | 0.67 | 0.31 |

Example 12: Effect of EHA/MMA/AA Concentration Ratio on Spore Removal

The formulations in Table 12 were prepared according to Example 10 above and tested according to Example 2 above. The formulations were stabilized with 3% DS-10.

TABLE 12

|  | 12-1 | 12-2 | 12-3 | 12-4 | 12-5 |
| --- | --- | --- | --- | --- | --- |
| 2-EHA/MMA/AA [73/25/2] | 0.000 | 0.000 | 2.000 | 0.000 | 0.000 |
| 2-EHA/MMA/AA [56/42/2] | 0.000 | 0.000 | 0.000 | 2.000 | 0.000 |
| 2-EHA/MMA/AA [25/73/2] | 0.000 | 0.000 | 0.000 | 0.000 | 2.000 |
| 1.0N NaOH | 0.000 | 0.000 | 0.470 | 0.402 | 0.254 |
| 200 Proof Ethanol | 0.000 | 70.000 | 70.000 | 70.000 | 70.000 |
| Water | 100.000 | 30.000 | 27.530 | 27.598 | 27.746 |
| pH |  |  | 7.18 | 7.13 | 7.14 |
| Log Reduction | 1.26 | 0.16 | 1.57 | 0.51 | 0.34 |
| Standard Deviation | 0.18 | 0.06 | 0.32 | 0.07 | 0.06 |

As seen from the data in Table 12, the 73/25/2 EHA: MMA AA provided the best spore removal performance.

Example 13

Example 13 was designed to determine the effect of increased concentrations of anionic surfactant, complemix, beyond what was used to stabilize the emulsion during preparation of the polymer, as well as the effect of other anionic surfactants and zwitter ionic surfactant that is used to stabilize emulsion for spore removal performance.

The formulations in Table 13 below were prepared according to Example 10 above and tested according to Example 2 above.

Samples 13-4 and 13-5 were very sticky. This made it difficult, at times, to rub the polyethylene glove bag across the Vitro-Skin sample. With this in mind there was an interesting trend observed where increasing Complemix concentration led to decreased spore removal. The use of anionic or zwitterionic surfactants to stabilize the acrylates achieved equivalent spore removal performance.

The data showed that increasing anionic surfactant (0.12% to 2.62%) showed lower spore removal. Also, the data showed that all anionic surfactants tested resulted in statistically similar spore removal.

Example 14

Example 14 was designed to determine the effect of the type of base in the formulation for spore removal performance as well as determine the effect of the acrylic acid concentration on spore removal performance.

The formulations in Table 14 below were prepared according to Example 10 above and tested according to Example 2 above.

TABLE 13

|  | 13-1 | 13-2 | 13-3 | 13-4 | 13-5 | 13-6 | 13-7 | 13-8 | 13-9 |
| --- | --- | --- | --- | --- | --- | --- | --- | --- | --- |
| 2-EHA/MMA (75/25), 3% Complemix 100 | 0.000 | 0.000 | 4.000 | 4.000 | 4.000 | 4.000 | 0.000 | 0.000 | 0.000 |
| 2-EHA/MMA (75/25), 3% Rhodical DS-10 | 0.000 | 0.000 | 0.000 | 0.000 | 0.000 | 0.000 | 4.000 | 0.000 | 0.000 |
| 2-EHA/MMA (75/25), 3% SDS | 0.000 | 0.000 | 0.000 | 0.000 | 0.000 | 0.000 | 0.000 | 4.000 | 0.000 |
| 2-EHA/MMA (75/25), 3% CAPB | 0.000 | 0.000 | 0.000 | 0.000 | 0.000 | 0.000 | 0.000 | 0.000 | 4.000 |
| Complemix 100 | 0.000 | 0.000 | 0.000 | 0.175 | 1.750 | 0.000 | 0.000 | 0.000 | 0.000 |
| 5 wt % 1N NaOH or 5 wt % 1N HCl | 0.000 | 0.000 | 4.460 | 4.460 | 4.460 | 4.460 | 0.167 | 0.132 | 0.333 |
| 200 proof Ethanol | 0.000 | 70.000 | 68.500 | 68.480 | 68.250 | 70.000 | 70.000 | 70.000 | 70.000 |
| Water | 100.000 | 30.000 | 23.040 | 22.885 | 21.540 | 21.540 | 25.834 | 25.868 | 25.667 |
| Total Complemix % | 0.00 | 0.00 | 0.12 | 0.295 | 1.87 | 0.12 | 0.000 | 0.00 | 0.00 |
| Final pH |  |  | 7.23 | 7.23 | 7.23 | 7.23 | 7.24 | 7.26 | 7.10 |
| Log Reduction | 1.11 | 0.3 | 2.27 | 1.09 | 0.036 | 2.41 | 2.33 | 2.14 | 2.34 |
| Standard Deviation | 0.14 | 0.04 |  |  |  | 0.09 | 0.19 | 0.21 | 0.10 |

TABLE 14

|  | 14-1 | 14-2 | 14-3 | 14-4 | 14-5 | 14-6 | 14-7 | 14-8 |
|---|---|---|---|---|---|---|---|---|
| 2-EHA/MMA/AA [70/22/8] | 0.000 | 0.000 | 2.000 | 2.004 | 0.000 | 0.000 | 13.329 | 0.000 |
| 2-EHA/MMA/AA [73/25/2] | 0.000 | 0.000 | 0.000 | 0.000 | 2.004 | 1.998 | 0.000 | 13.345 |
| 5 wt % 1N NaOH | 0.000 | 0.000 | 4.558 | 0.000 | 2.492 | 0.000 | 1.404 | 0.843 |
| TEA | 0.000 | 0.000 | 0.000 | 0.035 | 0.000 | 0.035 | 0.000 | 0.000 |
| 5 wt % 1N HCl | 0.000 | 0.000 | 0.000 | 0.150 | 0.000 | 1.000 | 0.000 | 0.000 |
| 200 Proof Ethanol | 0.000 | 70.000 | 70.000 | 70.040 | 70.060 | 70.007 | 69.993 | 70.395 |
| Water | 100.000 | 30.000 | 23.442 | 27.619 | 25.535 | 26.972 | 15.275 | 16.017 |
| pH |  |  | 7.2 | 7.2 | 7.19 | 7.21 | 7.2 | 7.23 |
| Log Reduction | 0.74 | 0.74 | 1.18 | 1.01 | 1.76 | 2.08 | 1.34 | 1.24 |

The data shows that an increased acrylic acid concentration decreased spore removal and there was no effect with a change of base to neutralize the acrylic acid (AA).

Example 15: Effect of a Quaternary Additive to Acrylate Formulation on Spore Removal The formulations in Table 15 below were prepared according to Example 10 above and tested according to Example 2 above.

TABLE 15

|  | 15-1 | 15-2 | 15-3 | 15-4 | 15-5 | 15-6 |
|---|---|---|---|---|---|---|
| 2-EHA/MMA/QMA [75/23/2] | 0.000 | 0.000 | 6.660 | 0.000 | 0.000 | 0.000 |
| 2-EHA/MMA/QMA [75/21/4] | 0.000 | 0.000 | 0.000 | 6.710 | 0.000 | 0.000 |
| 2-EHA/MMA/QMA [75/17/8] | 0.000 | 0.000 | 0.000 | 0.000 | 7.130 | 7.130 |
| Dermacryl C | 0.000 | 0.000 | 0.000 | 0.000 | 0.000 | 2.000 |
| 5 wt % 1N NaOH | 0.000 | 0.000 | 0.630 | 1.163 | 0.581 | 0.000 |
| 200 Proof Ethanol | 0.000 | 70.000 | 70.000 | 70.000 | 70.000 | 70.000 |
| Water | 100.000 | 30.000 | 23.340 | 23.290 | 22.870 | 20.870 |
| Log Reduction | 1.04 | 0.28 | 0.57 | 0.52 | 0.14 | 0.35 |
| Standard Deviation | 0.14 | 0.07 | 0.16 | 0.15 | 0.05 | 0.09 |

The data in Table 15 shows that the use of Quaternary additives to EHA/MMA formulations decreased removal of spores from synthetic skin.

Example 16: Evaluated the Use of Acrylate Polymers with Other Monomers for Spore Removal The formulations in Table 16 below were prepared according to Example 10 above and tested according to Example 2 above.

TABLE 16

|  | 16a-1 | 16a-2 | 16a-3 |
|---|---|---|---|
| IOA/BA/HEA [65/30/5] | 0.000 | 0.000 | 2.000 |
| CAHS | 0.000 | 0.000 | 1.000 |
| Centrimonium Bromide | 0.000 | 0.000 | 0.250 |
| 1.0N HCl | 0.000 | 0.000 | 0.744 |
| 1.0N NaOH | 0.000 | 0.000 | mix |
| 200 Proof Ethanol | 0.000 | 70.000 | 70.000 |
| Water | 100.000 | 30.000 | 23.442 |
| pH |  |  | 7.37 |
| Log Reduction | 1.38 | 0.29 | 0.45 |

|  | 16b-1 | 16b-2 | 16b-3 | 16b-4 |
|---|---|---|---|---|
| IOA/BA/HEMA/NMA [65/30/5/0.5] | 0.000 | 0.000 | 2.000 | 2.000 |
| CAHS | 0.000 | 0.000 | 1.000 | 0.000 |
| Centrimonium Bromide | 0.000 | 0.000 | 0.250 | 0.000 |
| 1.0N HCl | 0.000 | 0.000 | 0.000 | mix |
| 1.0N NaOH | 0.000 | 0.000 | 0.218 | 0.730 |
| 200 Proof Ethanol | 0.000 | 70.000 | 70.000 | 70.000 |
| Water | 100.000 | 30.000 | 26.532 | 27.270 |
| Log Reduction | 1.13 | 0.62 | 2.30 | 2.05 |

The data in Table 16 shows that the addition of NMA into IOA/BA/HEMA formulation increases spore removal.

Example 17: Effect of pH on 2-EHA/MMA-Complemix Solution on Spore Removal Performance The formulations in Table 17 below were prepared according to Example 10 above and tested according to Example 2 above.

TABLE 17

|  | 17-1 | 17-2 | 17-3 | 17-4 | 17-5 | 17-6 | 17-7 |
|---|---|---|---|---|---|---|---|
| 2-EHA/MMA [75/25] | 0.000 | 0.000 | 3.987 | 3.981 | 3.985 | 3.988 | 3.988 |
| 5 wt % NaOH | 0.000 | 0.000 | 0.000 | 3.195 | 4.375 | 8.069 | 5.015 |
| 200 Proof Ethanol | 0.000 | 70.000 | 69.899 | 69.910 | 70.039 | 69.910 | 70.000 |
| Water | 100.000 | 30.000 | 26.115 | 22.914 | 21.601 | 18.033 | 20.997 |
| pH |  |  | 3.58 | 4.58 | 5.50 | 6.45 | 7.60 |
| Log Reduction | 1.04 | 0.64 | 2.32 | 2.31 | 2.16 | 2.19 | 2.21 |
| Standard Deviation | 0.25 | 0.07 | 0.17 | 0.15 | 0.22 | 0.04 | 0.09 |

The data in Table 17 shows the effect of pH on the formula and suggests no statistical difference between pH 3.6 and 7.6 and the various points tested in between.

Example 18: The Effect of Increasing Concentrations of EHA/MMA (75/25) in 2% Complemix Formulations The formulations in Table 18 below were prepared according to Example 10 above and tested according to Example 2 above.

TABLE 18

|  | 18-1 | 18-2 | 18-3 | 18-4 | 18-5 | 18-6 |
|---|---|---|---|---|---|---|
| 2-EHA/MMA [75/25] | 0.00 | 0.00 | 0.20 | 0.51 | 0.99 | 2.00 |
| 5 wt % 1N NaOH | 0.00 | 0.00 | 1.00 | 0.82 | 0.78 | 1.06 |
| 200 Proof Ethanol | 0.00 | 70.00 | 70.00 | 70.00 | 70.00 | 70.00 |
| Water | 100.00 | 30.00 | 28.80 | 28.68 | 28.24 | 26.94 |
| pH |  |  | 7.3 | 7.2 | 7.3 | 7.2 |
| Log Reduction | 1.52 | 0.41 | 0.29 | 0.72 | 1.24 | 1.43 |
| Standard Deviation | 0.38 | 0.09 | 0.13 | 0.41 | 0.24 | 0.47 |

The data in Table 18 shows that an increase in removal of spores was observed as the concentration of EHA/MMA polymer was increased.

Example 19: The Effect of Adding Stearic Acid into Base Formulation (EHA/MMA (75/25) in 2% Complemix) in Order to Reduce Stickiness on Hands after Interaction with Formulation The formulations in Table 19 below were prepared according to Example 10 above and tested according to Example 2 above.

TABLE 19

|  | 19-1 | 19-2 | 19-3 | 19-4 |
|---|---|---|---|---|
| EHA/MMA [75/25] | 0.00 | 0.00 | 2.00 | 2.00 |
| Stearic Acid | 0.00 | 0.00 | 0.13 | 0.10 |
| Propylene Glycol | 0.00 | 0.00 | 0.52 | 0.00 |
| 200 Proof Ethanol | 0.00 | 70.00 | 70.00 | 70.00 |
| Water | 100.00 | 30.00 | 27.35 | 27.90 |
| Log Reduction | 1.52 | 0.41 | 1.97 | 1.59 |

Example 20: The Effect of Particle Size on Spore Removal

The size of the particles was determined in four different solvent systems: Water 100% (w/w); Ethanol/Water 30/70 (w/w); Ethanol/Water 70/30 (w/w); and Ethanol/Water 80/20 (w/w). A Solution of each solvent system was prepared in a 10 mL vial by mixing water and ethanol in the appropriate weight rations. These solutions were used to dilute the polymer samples for analysis. The refractive index of each of these solvent system solutions was measured on a Rudolph J357 Automatic Refractometer at 25.0° C. The refractive index of the diluent is needed as an input parameter for the particle size analysis.

Each polymer solution was then diluted by addition of one drop of polymer solution (~0.05 g) to a plastic cuvet (Plastibrand disposable cuvets, 2.5 mL macro, 12.5×12.5× 45 mm, ISO 9001-14001 Certified, Cat. #759070D), followed by ~2 mL of the appropriate diluent. The diluted sample should be clear to slightly hazy. The diluted sample cuvet was the placed into the cuvet-holder of a Coulter Model N4 MD Sub-Micron Particle Analyzer. Proper dilution of the polymer was verified by going to the "Sample Preparation" tab and checking the sample intensity. The instrument displays a "counts/second" value that must be between 5.00 E+04 and 1.00 E+06 counts/sec for the instrument to properly analyze the sample. If the sample was outside of this range then a new sample was prepared so that the intensity was in the proper range.

The following parameters were input and the samples analyzed:
Temperature=20° C.
Viscosity=0.01 poise
Refractive Index=[Parameter measured above for each diluent]
Angle=90.0 degrees
Sample Time=5.0 microsecond
Pre-Scale=2
Run Time=60 seconds The data output of the instrument shows modality of the distribution, the mean diameter, the 95% limits, and the standard deviation. The particle size is seen in Table 20a below. The ability of the solutions to remove spores were also tested as described in Example 2 above and are given in Table 20b.

TABLE 20a

| Sample | Solution (w/w) | Mean Diameter (nm) | 95% Limits (nm) | Standard Deviation (nm) |
|---|---|---|---|---|
| 0% Ethanol (20-3) | Water 100% | 69.7 | 67.0-72.5 | 15 |
| 30% Ethanol (20-4) | EtOH/Water 30/70 | 173 | 162-183 | Narrow |
| 70% Ethanol (20-5) | EtOH/Water 70/30 | 331 | 303-359 | Narrow |
| 80% Ethanol (20-6) | EtOH/Water 80/20 | 501 | 449-552 | Narrow |

TABLE 20b

|  | 20-1 | 20-2 | 20-3 | 20-4 | 20-5 | 20-6 |
|---|---|---|---|---|---|---|
| 2-EHA/MMA [75/25] | 0.00 | 0.00 | 3.97 | 3.97 | 3.97 | 3.98 |
| 200 Proof Ethanol | 0.00 | 70.00 | 0.00 | 30.00 | 69.97 | 80.32 |
| Water | 100.00 | 30.00 | 96.03 | 66.03 | 20.06 | 15.7 |
| pH |  |  | Between 6.5 to 7 |  |  |  |
| Log Reduction | 0.79 | 0.22 | 0.32 | 0.85 | 1.98 | 0.72 |
| Standard Deviation | 0.14 | 0.11 | 0.49 | 0.15 | 0.15 | 0.25 |

Example 21: Effect of Drying of Ethanol on Particle Size and Spore Removal

In this experiment, ethanol in sample 20-5 that was prepared in example 20 was allowed to evaporate overnight. The loss of ethanol was compensated by water. This sample was called sample 21-5 and was tested for particle size and for spore removal testing as described in Example 20. The data is given in Tables 21a and 21b below.

TABLE 21a

| Sample | Solution (w/w) | Mean Diameter (nm) | 95% Limits (nm) | Standard Deviation (nm) |
|---|---|---|---|---|
| 0% Ethanol, (21-2) | Water 100% | 75.3 | 72.2-78.3 | Narrow |
| 70% Ethanol, (21-3) | EtOH/Water 70/30 | 598 | 531-665 | Narrow |

TABLE 21a-continued

| Sample | Solution (w/w) | Mean Diameter (nm) | 95% Limits (nm) | Standard Deviation (nm) |
|---|---|---|---|---|
| Ethanol evaporated, water added (21-5) | Water 100% | 170 | 160-180 | 40 |
| Ethanol evaporated (21-4) | Water 100% | 171 | 160-181 | 47 |

TABLE 21b

|  | 21-1 | 21-2 | 21-3 | 21-4* | 21-5** |
|---|---|---|---|---|---|
| 2-EHA/MMA [75/25] | 0.00 | 3.99 | 3.97 | 13.44 | 4.01 |
| 200 Proof Ethanol | 70.00 | 0.00 | 69.98 | 0.00 | 0.00 |
| Water | 30.00 | 96.01 | 26.05 | 86.56 | 95.99 |
| pH |  |  | Between 6.5 to 7 |  |  |
| Log Reduction | 0.56 | 1.35 | 1.62 | 2.17 | 1.9 |
| Standard Deviation | 0.2 | 0.26 | 0.22 | 0.56 | 0.23 |

*Formula 21-4 was made by evaporating the ethanol off of a sample with the same composition as 21-3
**Formula 21-5 was made the same way as formula 21-4 only after the ethanol was evaporated water was added to decrease the concentration of 2-EHA/MMA to near 4%

Thus, embodiments of compositions for spore removal are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation.

The invention claimed is:

1. A composition comprising:

a) at least 85 wt % of a hydroalcoholic solution, the hydroalcoholic solution comprising:

at least 1 wt % water based on the total weight of the hydroalcoholic solution; and 30 wt % to 85 wt % of at least one $C_1$ to $C_4$ alkyl alcohol based on the total weight of the hydroalcoholic solution; and b) acrylate copolymer particles dispersed in the hydroalcoholic solution, the acrylate copolymer particles comprising the reaction product of a reaction mixture, the reaction mixture comprising monomers, the monomers comprising:

from 5 wt % to 50 wt % of at least one high Tg monomer having an alkyl carbon chain length in a range from 1 to 3, and having a Tg from 40° C. to 150° C., where the wt % of the high Tg monomer is with respect to the total weight of the monomers in the reaction mixture; and from 20 wt % to 80 wt % of at least one low Tg monomer having an alkyl carbon chain length of at least 4 and having a Tg from −20° C. to −60° C. where the wt % of the low Tg monomer is with respect to the total weight of the monomers in the reaction mixture, wherein the particles have a number average diameter of at least 100 nm and not greater than 500 nm.

2. The composition according to claim 1, wherein there is more of the at least one low Tg monomer than there is of the at least one high Tg monomer by weight in the reaction mixture.

3. The composition according to claim 1, wherein there is not greater than 5 wt % of the acrylate copolymer particles in the composition based on the total weight of the composition.

4. The composition according to claim 1, wherein there is from 0.5 wt % to 4 wt % of the acrylate copolymer particles in the composition based on the total weight of the composition.

5. The composition according to claim 1, wherein there is at least 60 wt % of the at least one alcohol in the composition based on the total weight of the composition.

6. The composition according to claim 1, wherein the acrylate copolymer is the reaction product of 20 wt % to 40 wt % of the at least one high Tg monomer based on the total weight of the monomers in the reaction mixture.

7. The composition according to claim 1, wherein the acrylate copolymer is the reaction product of 60 wt % to 80 wt % of the at least one low Tg monomer based on the total weight of the monomers in the reaction mixture.

8. The composition according to claim 1, wherein the at least one low Tg monomer has an alkyl carbon chain length from 4 to 10.

9. The composition according to claim 1, wherein the acrylate copolymer particles have a number average diameter from 200 to 500 nm.

10. The composition according to claim 1, wherein the at least one $C_1$ to $C_4$ alcohol is selected from ethanol, n-propanol, 2-propanol or mixtures thereof.

11. The composition according to claim 1 further comprising an antimicrobial agent in addition to the alcohol.

12. The composition according to claim 11, wherein the antimicrobial agent is cationic.

13. A composition comprising:

at least 1 wt % water based on the total weight of the composition;

from 85 wt % to 98 wt % of at least one $C_1$ to $C_4$ alkyl alcohol based on the total weight of the composition; and 0.5 TO 4.0 wt % acrylate copolymer particles based on the total weight of the composition, where the acrylate copolymer particles are dispersed in the water and alcohol, the acrylate copolymer particles comprising the reaction product of a reaction mixture, the reaction mixture comprising monomers, the monomers comprising:

from 5 wt % to 50 wt % of at least one high Tg monomer having an alkyl carbon chain length in a range from 1 to 3, and having a Tg from 40° C. to 150° C., where the wt % of the high Tg monomer is with respect to the total weight of the monomers in the reaction mixture; and from 20 wt % to 80 wt % of at least one low Tg monomer having an alkyl carbon chain length of at least 4 and having a Tg from −20° C. to −60° C., where the wt % of the low Tg monomer is with respect to the total weight of the monomers in the reaction mixture, wherein the particles have a number average diameter of at least 100 nm and not greater than 500 nm.

14. A method of removing at least one spore from a surface, the method comprising:

contacting the surface with a composition, the composition comprising:

at least 85 wt % of a hydroalcoholic solution based on the total weight of the composition, the hydroalcoholic solution comprising:

at least 1 wt % water based on the weight of the hydroalcoholic solution, and 30 wt % to 95 wt % of at least one $C_1$ to $C_4$ alkyl alcohol based on the total weight of the hydroalcoholic solution; and acrylate copolymer particles dispersed in the hydroalcoholic solution, the acrylate copolymer particles comprising the reaction product of a reaction mixture, the reaction mixture comprising monomers, the monomers comprising:
- from 5 wt % to 50 wt % of at least one high Tg monomer having an alkyl carbon chain length in a range from 1 to 3, and having a Tg from 40° C. to 150° C., where the wt % of the at least one high Tg monomer is with respect to the total weight of the monomers in the reaction mixture; and
- from 20 w % to 80 wt % of at least one low Tg monomer having an alkyl carbon chain length of at least 4 and having a Tg from −20° C. to −60° C., where the wt % of the at least one low Tg monomer is with respect to the total weight of the monomers in the reaction mixture, wherein the acrylate copolymer particles have an average diameter of at least 100 nm and not greater than 500 nm.

15. The method according to claim 14, wherein the surface is dipped in the composition.

16. The method according to claim 14, wherein the composition is applied to the surface.

17. The method according to claim 14 further comprising removing at least a portion of the composition, wherein removing at least a portion of the composition removes at least one spore from the surface.

18. The method according to claim 17, wherein the step of removing at least a portion of the composition comprises mechanical action.

19. The method according to claim 14, wherein the surface comprises skin.

* * * * *

UNITED STATES PATENT AND TRADEMARK OFFICE
CERTIFICATE OF CORRECTION

PATENT NO. : 10,555,889 B2
APPLICATION NO. : 15/736853
DATED : February 11, 2020
INVENTOR(S) : Parthasarathy et al.

It is certified that error appears in the above-identified patent and that said Letters Patent is hereby corrected as shown below:

On the Title Page

Item (57), Abstract:
Column 2, Line 10, delete "w %" and insert -- wt% --

In the Specification

Column 2, Line 26, delete "w %" and insert -- wt% --

Column 8, Line 59, delete "(vinyl pyrolidinone/Eicosenene" and insert -- (vinylpyrrolidinone / Eicosene --

Column 9, Line 10, delete "cetyl pyridinium" and insert -- cetylpyridinium --

Column 11, Line 6, delete "sufonates" and insert -- sulfonates --

Column 11, Line 67, delete "Parsipanny" and insert -- Parsippany --

Column 12, Line 1, delete "Rhodocal" and insert -- Rhodacal --

Column 12, Line 38, delete "lauraniinopropionic" and insert -- lauraminopropionic --

Column 12, Line 44, delete "RI7-" and insert -- R17 --

Column 12, Line 45, delete "—RI8-N+(RI9)$_2$" and insert -- —R18-N+(R19)$_2$ --

Column 22, Line 7, delete "37 C" and insert -- 37° C. --

Column 22, Lines 23-24, delete ""Eudrajit" and insert -- Eudragit --

Signed and Sealed this
Nineteenth Day of April, 2022

Katherine Kelly Vidal
*Director of the United States Patent and Trademark Office*

CERTIFICATE OF CORRECTION (continued)
U.S. Pat. No. 10,555,889 B2

Column 29, Line 29, delete "zwitter ionic" and insert -- zwitterionic --

Column 29, Line 45, delete "Rhodical" and insert -- Rhodacal --

Column 32, Line 24, delete "Centrimonium" and insert -- Cetrimonium --

Column 32, Line 36, delete "Centrimonium" and insert -- Cetrimonium --

In the Claims

Column 36, Line 35, delete "TO" and insert -- to --

Column 37, Line 12, delete "w %" and insert -- wt% --